(12) United States Patent
Kurihara et al.

(10) Patent No.: US 11,510,971 B2
(45) Date of Patent: Nov. 29, 2022

(54) IMMUNE INDUCER

(71) Applicant: TORAY INDUSTRIES, INC., Tokyo (JP)

(72) Inventors: Akira Kurihara, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 585 days.

(21) Appl. No.: 15/743,869

(22) PCT Filed: Aug. 5, 2016

(86) PCT No.: PCT/JP2016/073077
§ 371 (c)(1),
(2) Date: Jan. 11, 2018

(87) PCT Pub. No.: WO2017/026389
PCT Pub. Date: Feb. 16, 2017

(65) Prior Publication Data
US 2018/0200356 A1 Jul. 19, 2018

(30) Foreign Application Priority Data
Aug. 10, 2015 (JP) .............................. JP2015-158539

(51) Int. Cl.
| | | |
|---|---|---|
| *A61K 39/00* | (2006.01) | |
| *C07K 14/47* | (2006.01) | |
| *A61K 45/00* | (2006.01) | |
| *A61K 48/00* | (2006.01) | |
| *A61K 39/39* | (2006.01) | |
| *C12N 5/10* | (2006.01) | |
| *C12N 15/09* | (2006.01) | |
| *A61K 35/15* | (2015.01) | |
| *A61K 35/76* | (2015.01) | |
| *A61K 35/17* | (2015.01) | |
| *A61P 35/00* | (2006.01) | |

(52) U.S. Cl.
CPC .......... *A61K 39/0011* (2013.01); *A61K 35/15* (2013.01); *A61K 35/17* (2013.01); *A61K 35/76* (2013.01); *A61K 39/00* (2013.01); *A61K 39/39* (2013.01); *A61K 45/00* (2013.01); *A61K 48/00* (2013.01); *A61P 35/00* (2018.01); *C07K 14/47* (2013.01); *C07K 14/4702* (2013.01); *C12N 5/10* (2013.01); *C12N 15/09* (2013.01); *A61K 2039/5154* (2013.01); *A61K 2039/5158* (2013.01); *A61K 2039/53* (2013.01); *A61K 2039/572* (2013.01)

(58) Field of Classification Search
None
See application file for complete search history.

(56) References Cited

U.S. PATENT DOCUMENTS

| | | | | |
|---|---|---|---|---|
| 7,842,467 | B1 * | 11/2010 | Heidbrink | ............... A61P 35/00 435/7.1 |
| 2004/0248218 | A1 | 12/2004 | Kasid et al. | |
| 2012/0177673 | A1 | 7/2012 | Kurihara et al. | |

FOREIGN PATENT DOCUMENTS

| | | |
|---|---|---|
| CN | 102481333 A | 5/2012 |
| EP | 2 213 301 A1 | 8/2010 |
| EP | 2 474 315 A1 | 7/2012 |
| RU | 2 529 373 C2 | 9/2012 |
| WO | WO 02/081641 A2 | 10/2002 |
| WO | WO 2009/0544710 A1 | 4/2009 |
| WO | WO 2010/021112 A1 | 2/2010 |
| WO | WO 2011/027807 A1 | 3/2011 |
| WO | WO 2017/184590 A8 | 10/2017 |

OTHER PUBLICATIONS

Hassan et al (Molecular & Cellular Proteomics, 2013, 10.74/mcp. M112.024810: 1829-1843) (Year: 2013).*
Caron et al (eLife, 7/15, 4:e07661, pp. 1-17) (Year: 2015).*
Kerkar and Restifo (Cancer Res.2012, 72(13): 3125-3130) (Year: 2012).*
Vitale et al. (Eur. J. Immunol. 2014, 44: 1582-1592) (Year: 2014).*
DiBrino et al (J. Immunology 151(11) 5930-5935, 1993) (Year: 1993).*
Celis et al (Mol. Immunol. 1994, 31(18): 1423-1430) (Year: 1994).*
HLA Nomenclature (Year: 2015).*
Speiser et al (Eur. J. Immunol. 2002, 32: 731-741) (Year: 2002).*
Berger et al. (Int. J. Cancer. 111: 229-237, 2004) (Year: 2004).*
Kalos and June (Immunity, 2013, 39: 49-60) (Year: 2013).*
Spranger, S (Int. Immunol. 2015, 28(8): 383-391) (Year: 2015).*
Beatty and Gladney (Clin. Canc. Res. 2014, 21(4): 687-692) (Year: 2014).*
Engelhard, V.H. (Curr. Opin. Immunol. 1994, 6: 13-23) (Year: 1994).*

(Continued)

*Primary Examiner* — G. R. Ewoldt
*Assistant Examiner* — Marianne DiBrino
(74) *Attorney, Agent, or Firm* — Birch, Stewart, Kolasch & Birch, LLP

(57) ABSTRACT

An object of the present invention is to discover a novel peptide useful as an active ingredient in an agent for treating or preventing cancer, and to provide the use of the polypeptide as an immune inducer. The immune inducer contains as an active ingredient, the following (i) or (ii): (i) at least one polypeptide having an immune-inducing activity and selected from the group of polypeptides (a) or (b), where: (a) polypeptides consisting of 7 or more consecutive amino acids within the region of positions 24 to 97 in the amino acid sequence represented by SEQ ID NO: 2; and (b) polypeptides comprising one to several amino acid deletions, substitutions and/or additions in the amino acid sequence of any one of the polypeptides (a); and (ii) a recombinant vector comprising at least one polynucleotide encoding any one of the polypeptides, and capable of expressing the polypeptide in vivo.

1 Claim, 8 Drawing Sheets

Specification includes a Sequence Listing.

(56) References Cited

OTHER PUBLICATIONS

Guo et al (Nature, 1992, 360: 364-366) (Year: 1992).*
Eisenlohr et al (J. Exp. Med. 1992, 175: 481-487) (Year: 1992).*
Shastri et al (J. Immunol. 1995, 155: 4339-4346) (Year: 1995).*
Bergmann et al (J. Immunol. 1996, 157: 3242-3249) (Year: 1996).*
Wang et al (Cell. Immunol. 1992, 143: 284-297) (Year: 1992).*
Theoboald et al (J. Exp. Med. 1998, 188(6): 1017-1028) (Year: 1998).*
Gileadi et al (Eur. J. Immunol. 1999, 29: 2213-2222) (Year: 1999).*
Wieczorek et al. (Front. Immunol. 2017, vol. 8, article 292: 1-16) (Year: 2017).*
Reche and Reinherz (G. Nicosia etal, Eds. ICARIS 2004, LNCS 3239: 189-196) (Year: 2004).*
Bourdetsky et al. (PNAS, publ. online Apr. 8, 2014, E1591-E1599) (Year: 2014).*
FastSEQ (Year: 2021).*
Kumar et al. "SCC-112, a novel cell cycle-regulated molecule, exhibits reduced expression in human renal carcinomas", Gene, 2004, vol. 328, pp. 187-196.
Extended European Search Report dated Feb. 22, 2019, in European Patent Application No. 16835086.6.
Put et al., " PDS5A, a novel translocation partner of MLL in acute myeloid leukemia," Leukemia Research (2012), vol. 36, pp. e87-e89.
Office Action dated Jan. 31, 2020, in Russian Patent Appication No. 2018107330/10(011202).
Office Action dated Nov. 19, 2020, in Russian Patent Application No. 2018107330/10(011202).
Communication Pursuant to Article 94(3) EPC dated Sep. 2, 2020, in EP 16 835 086.6.
English translation of Office Action dated Sep. 2, 2020, in Chinese Patent Application No. 201680043484.5.
Roit, I. et al. (2003) Immunology 5th Edition, St. Louis, Missouri: J.P. Lippincott, pp. 114-117.
English translation of Written Opinion of the International Searching Authority dated Sep. 20, 2016, in PCT/JP2016/073077.
International Search Report, issued in PCT/JP2016/073077, PCT/ISA/210, dated September 20, 2016.

* cited by examiner

IMMUNE INDUCER

REFERENCE TO SEQUENCE LISTING SUBMITTED VIA EFS-WEB

This application includes an electronically submitted sequence listing in .txt format. The .txt file contains a sequence listing entitled "2018-01-11-SEQ-LISTING-1254-0602PUS1.txt" created on Jan. 11, 2018 and is 50,488 bytes in size. The sequence listing contained in this .txt file is part of the specification and is hereby incorporated by reference herein in its entirety.

TECHNICAL FIELD

The present invention relates to a novel immune inducer useful as an active ingredient in an agent for treating or preventing cancer.

BACKGROUND ART

PDS5A (PDS5, regulator of cohesion maintenance, homolog A) protein, also known as SSC-112, is a protein identified as a cell cycle regulator involved in the distribution of chromosomes.

PDS5A protein has been suggested to be associated with the development of cancer. For example, Patent Literature 1 discloses that the expression of PDS5A protein is higher in nasopharyngeal cancer, renal cancer, liver cancer and one type of breast cancer cells as compared to normal tissue. Further, Patent Literature 1 also discloses that the proliferation of cancer cells can be inhibited by suppressing the expression of PDS5A protein in the cancer cells using an antisense nucleic acid, ribozyme or siRNA against PDS5A gene, or an anti-PDS5A protein antibody, and that it can induce apoptosis in cancer cells by administering the full-length PDS5A protein or a partial peptide of the protein.

Patent Literature 2 discloses that the PDS5A protein that bind to HLA-A0201, which is a subtype of MHC class I molecules, and partial peptides thereof have an immune-inducing activity against cancer cells, and thus are useful for treatment and/or prevention of cancer. However, Patent Literature 2 does not disclose all the peptides that bind to HLA-A0201, nor information on peptides that bind to subtypes other than HLA-A0201.

CITATION LIST

Patent Literature

Patent Literature 1: WO 2002/081641
Patent Literature 2: WO 2011/027807

SUMMARY OF INVENTION

Technical Problem

An object of the present invention is to find a novel polypeptide useful as an active ingredient in an agent for treating or preventing cancer, and to provide the use of the polypeptide as an immune inducer.

Another object of the present invention is to provide an isolated antigen-presenting cell including a complex of the polypeptide and an HLA molecule, and an isolated T cell which selectively binds to a complex of the polypeptide and an HLA molecule, as well as an agent for treating or preventing cancer including the same.

Solution to Problem

As a result of intensive research, the present inventors have found that the human PDS5A protein consisting of the amino acid sequence represented by SEQ ID NO: 2 is specifically expressed in tissues or cells of leukemia, malignant lymphoma, breast cancer, liver cancer, prostate cancer, pancreatic cancer, ovarian cancer, renal cancer, colorectal cancer, stomach cancer, malignant brain tumor, esophageal cancer, and lung cancer. Further, the inventors have found out that a partial peptide present in a specific region of the PDS5A protein has an ability (immune-inducing activity) to activate and propagate T cells specific to the polypeptide via the presentation by the antigen-presenting cells, and that the immune-inducing activity is useful for the treating or preventing cancer. Based on these findings, the inventors have found out that the polypeptide can be used as an active ingredient in an immune inducer for treating and/or preventing cancer, and that antigen-presenting cells which have been in contact with the peptide, and T cells which have been in contact with the antigen-presenting cells are also useful in the treatment or prevention of cancer, thereby completing the present invention.

Specifically, the present invention has the following characteristics (1) to (14).

(1) An immune inducer comprising, as an active ingredient, the following (i) or (ii):
 (i) at least one polypeptide having an immune-inducing activity and selected from the group of polypeptides (a) or (b) below:
  (a) polypeptides consisting of seven or more consecutive amino acids within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 and positions 1074 to 1215 in the amino acid sequence represented by SEQ ID NO: 2;
  (b) polypeptides comprising one to several amino acid deletions, substitutions and/or additions in the amino acid sequence of any one of the polypeptides (a);
 (ii) a recombinant vector comprising at least one polynucleotide encoding any one of the polypeptides, and capable of expressing the polypeptide in vivo.

(2) The immune inducer according to (1), wherein the polypeptide (i) binds to a MHC class I molecule.

(3) The immune inducer according to (2), wherein the polypeptide (i) is any one of the polypeptides selected from the group of polypeptides (c) to (e) below:
 (c) polypeptides consisting of the amino acid sequences represented by SEQ ID NOs: 3 to 34;
 (d) polypeptides comprising one to several amino acid deletions, substitutions and/or additions in the amino acid sequence of any one of the polypeptides (c);
 (e) polypeptides each comprising as a partial sequence any one of the polypeptides (c) or (d).

(4) The immune inducer according to (1), wherein the polypeptide (i) binds to a MHC class II molecule.

(5) The immune inducer according to (4), wherein the polypeptide (i) is any one of the polypeptides selected from the group of polypeptides (0 to (h) below:

(0 polypeptides consisting of the amino acid sequences represented by SEQ ID NOs: 35 to 67;

(g) polypeptides comprising one to several amino acid deletions, substitutions and/or additions in the amino acid sequence of any one of the polypeptides (0;

(h) polypeptides each comprising as a partial sequence any one of the polypeptides (f) or (g).

(6) The immune inducer according to any one of (1) to (5), which is used as an active ingredient in an agent for treating or preventing cancer.

(7) The immune inducer according to (6), wherein the cancer is a cancer expressing PDS5A protein.

(8) The immune inducer according to any one of (6) or (7), wherein the cancer is leukemia, malignant lymphoma, prostate cancer, liver cancer, breast cancer, pancreatic cancer, ovarian cancer, renal cancer, colorectal cancer, stomach cancer, malignant brain tumor, lung cancer or esophageal cancer.

(9) The immune inducer, according to any one of (1) to (8), further comprising an immunopotentiator.

(10) A polypeptide having an immune-inducing activity and selected from the group of polypeptides (a) or (b) below:

(a) polypeptides having an immune-inducing activity and consisting of 7 or more consecutive amino acids within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 and positions 1074 to 1215 in the amino acid sequence represented by SEQ ID NO: 2;

(b) polypeptides comprising one to several amino acid deletions, substitutions and/or additions in the amino acid sequence of any one of the polypeptides (a).

(11) The polypeptide according to (10), wherein the polypeptide is any one polypeptide selected from the group of polypeptides (c) to (e) below:

(c) polypeptides consisting of the amino acid sequences represented by SEQ ID NOs: 3 to 34;

(d) polypeptides comprising one to several amino acid deletions, substitutions and/or additions in the amino acid sequence of any one of the polypeptides (c);

(e) polypeptides each comprising as a partial sequence any one of the polypeptides (c) or (d).

(12) The polypeptide according to (10), wherein the polypeptide is any one polypeptide selected from the group of polypeptides (0 to (h) below:

(f) polypeptides consisting of the amino acid sequences represented by SEQ ID NOs: 35 to 67;

(g) polypeptides comprising one to several amino acids deletions, substitutions and/or additions in the amino acid sequence of any one of the polypeptides (f);

(h) polypeptides each comprising as a partial sequence any one of the polypeptides (f) or (g).

(13) An isolated antigen-presenting cell comprising a complex of the polypeptide having an immune-inducing activity according to any one of (10) to (12) and a MHC molecule.

(14) An isolated T cell which selectively binds to a complex of the polypeptide having an immune-inducing activity according to any one of (10) to (12) and a MHC molecule.

The present specification encompasses the disclosure of Japanese Patent Application No. 2015-158539 to which the present application claims priority.

Effects of Invention

The present invention provides a novel immune inducer useful as an active ingredient in an agent for treating or preventing cancer.

Further, as specifically shown in Examples to be described later, the polypeptides used in the present invention can induce immune cells that kill cancer cells, thereby enabling the reduction in size or regression of an already existing cancer. In addition, the peptides used in the present invention can also enhance the induction of the immune cells that kill cancer cells, and thereby enabling the reduction in size or regression of an already existing cancer. Therefore, the polypeptides according to the present invention are useful as an active ingredient in an agent for treating or preventing cancer.

BRIEF DESCRIPTION OF DRAWINGS

In FIG. 2, Lanes 13 to 29 on the horizontal axis show the IFN-γ-producing abilities of HLA-A0201-positive CD8-positive T cells in response to stimulation by dendritic cells pulsed with the polypeptides having the amino acid sequences represented by SEQ ID NOs: 3 to 19, respectively. Lane 1 shows the result obtained when the above treatment was carried out without adding any polypeptide (Mock); Lane 2 shows the result obtained when the above treatment was carried out with the addition of a negative control polypeptide having the amino acid sequence represented by SEQ ID NO: 74, which is outside the scope of the present invention; Lane 3 shows the result obtained when the above treatment was carried out with the addition of the full-length PDS5A protein consisting of the amino acid sequence represented by SEQ ID NO: 2; and Lanes 4 to 12 show the results obtained when the above treatment was carried out with the addition of polypeptides having the amino acid sequences represented by SEQ ID NOs: 75 to 83, respectively, which are outside the scope of the present invention.

In FIG. 3, Lanes 4 to 18 on the horizontal axis show the IFN-γ-producing abilities of HLA-A24-positive CD8-positive T cells in response to stimulation by dendritic cells pulsed with the polypeptides having the amino acid sequences represented by SEQ ID NOs: 20 to 34, respectively. Lane 1 shows the result obtained when the above treatment was carried out without adding any polypeptide (Mock); Lane 2 shows the result obtained when the above treatment was carried out with the addition of a negative control peptide having the amino acid sequence represented by SEQ ID NO: 84, which is outside the scope of the present invention; and Lane 3 shows the result obtained when the above treatment was carried out with the addition of the full-length PDS5A protein consisting of the amino acid sequence represented by SEQ ID NO: 2.

In FIG. 4A, Lanes 13 to 29 on the horizontal axis show the cytotoxic activities, against U251 cells, of HLA-A0201-positive CD8-positive T cells induced using the polypeptides having the amino acid sequences represented by SEQ ID NOs: 3 to 19, respectively. Lane 1 shows the cytotoxic activity of CD8-positive T cells (Mock) induced without adding any polypeptide; Lane 2 shows the cytotoxic activity of CD8-positive T cells induced using the negative control polypeptide (SEQ ID NO: 74); Lane 3 shows the cytotoxic activity of CD8-positive T cells induced using the full-length PDS5A protein consisting of the amino acid sequence represented by SEQ ID NO: 2; and Lanes 4 to 12 show the cytotoxic activities of CD8-positive T cells induced using the polypeptides having the amino acid sequences represented by SEQ ID NOs: 75 to 83, respectively, which are outside the scope of the present invention.

In FIG. 4B, Lanes 12 to 28 on the horizontal axis show the cytotoxic activities, against Jurkat cells, of HLA-A0201-positive CD8-positive T cells induced using the polypeptides having the amino acid sequences represented by SEQ ID NOs: 3 to 19, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 74); Lane 3 shows the cytotoxic activity of the CD8-positive T cells induced using the full-length PDS5A protein consisting of the amino acid sequence represented by SEQ ID NO: 2; and Lanes 4 to 11 show the cytotoxic activities of CD8-positive T cells induced using the polypeptides having the amino acid sequences represented by SEQ ID NOs: 75 to 83, respectively, which are outside the scope of the present invention.

In FIG. 5A, Lanes 4 to 18 on the horizontal axis show the cytotoxic activities, against THP1 cells, of HLA-A24-positive CD8-positive T cells stimulated using the polypeptides having the amino acid sequences represented by SEQ ID NOs: 20 to 34, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 84); and Lane 3 shows the cytotoxic activity of the CD8-positive T cells induced using the PDS5A protein consisting of the amino acid sequence represented by SEQ ID NO: 2.

In FIG. 5B, Lanes 4 to 18 on the horizontal axis show the cytotoxic activities, against SW480 cells, of the HLA-A24-positive CD8-positive T cells stimulated using the polypeptides having the amino acid sequences represented by SEQ ID NOs: 20 to 34, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 84); and Lane 3 shows the cytotoxic activity of the CD8-positive T cells induced using the PDS5A protein consisting of the amino acid sequence represented by SEQ ID NO: 2.

In FIG. 6, Lanes 4 to 36 on the horizontal axis show the IFN-γ-producing abilities of HLA-DRB1*04-positive CD4-positive T cells in response to stimulation by dendritic cells pulsed with the polypeptides having the amino acid sequences represented by SEQ ID NOs: 35 to 67, respectively. Lane 1 shows the result obtained when the above treatment was carried out without adding any polypeptide (Mock); Lane 2 shows the result obtained when the above treatment was carried out with the addition of a negative control polypeptide having the amino acid sequence represented by SEQ ID NO: 85, which is outside the scope of the present invention; and Lane 3 shows the result obtained when the above treatment was carried out with the addition of the full-length PDS5A protein consisting of the amino acid sequence represented by SEQ ID NO: 2.

DESCRIPTION OF EMBODIMENTS

<Polypeptide>

Figure 1:
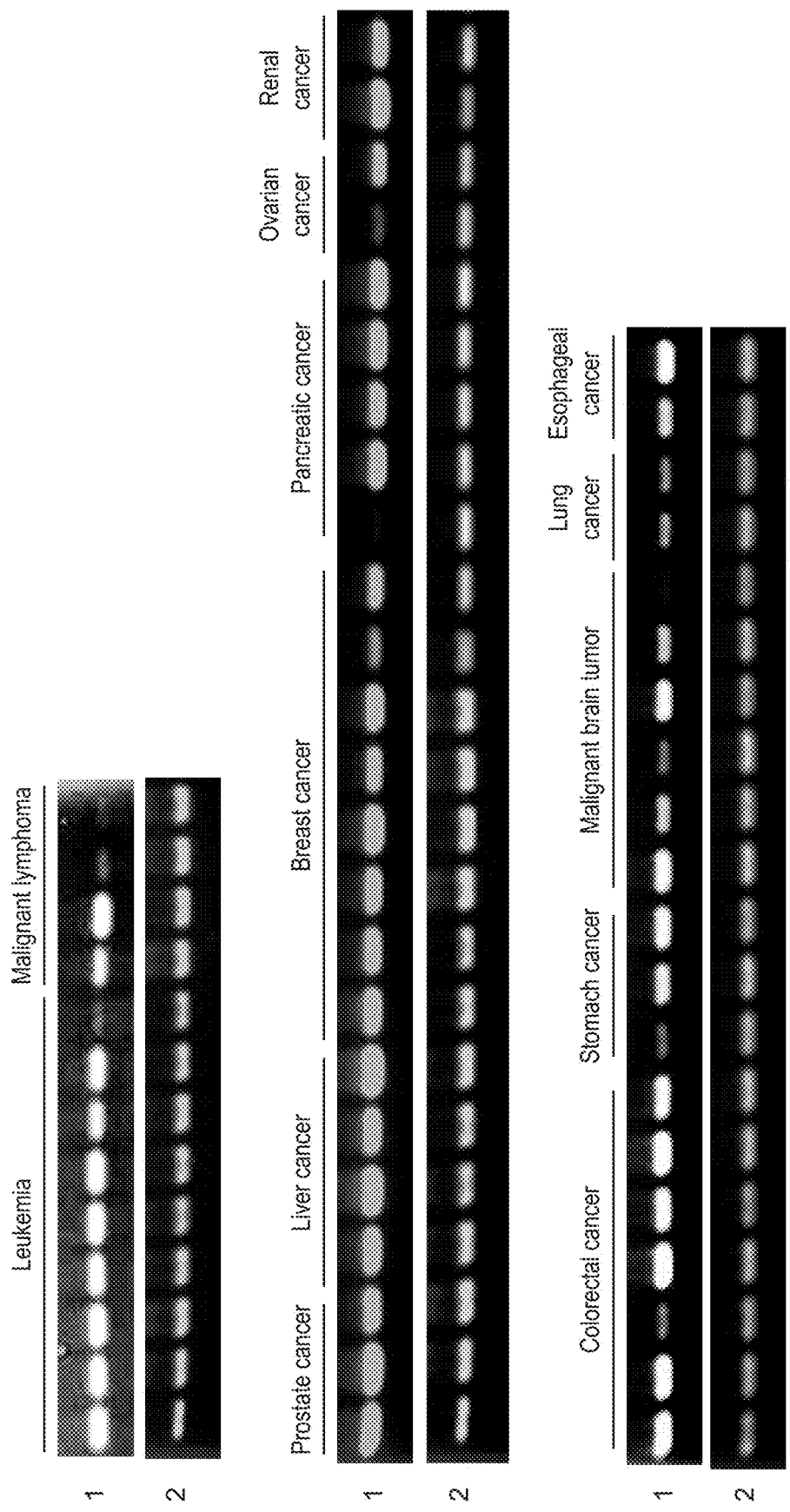
FIG. 1 shows the expression patterns of PDS5A gene, in human tumor tissues and cancer cell lines. Reference number 1 indicates the expression pattern of the human PDS5A gene. Reference number 2 indicates the expression pattern of human GAPDH gene, which is a human housekeeping gene.

In the present invention, the term "polypeptide" refers to a molecule formed by peptide bonding of a plurality of amino acids. The polypeptides according to the present invention include not only polypeptide molecules composed of a large number of amino acids but also low-molecular-weight molecules (oligopeptides) composed of a small number of amino acids.

The polypeptide constituting the immune inducer according to the present invention may be, for example, at least one polypeptide having an immune-inducing activity and selected from the group of polypeptides (a) or (b) below:

(a) polypeptides consisting of 7 or more consecutive amino acids within the region of positions 24 to 97 (74 amino acids), positions 113 to 132 (20 amino acids), positions 134 to 197 (64 amino acids), positions 204 to 225 (22 amino acids), positions 265 to 332 (68 amino acids), positions 378 to 463 (86 amino acids), positions 472 to 498 (27 amino acids), positions 533 to 567 (35 amino acids), positions 613 to 643 (31 amino acids), positions 671 to 735 (65 amino acids), positions 737 to 780 (44 amino acids), positions 792 to 830 (39 amino acids), positions 832 to 899 (68 amino acids), positions 920 to 943 (24 amino acids), positions 946 to 993 (58 amino acids), positions 1029 to 1069 (41 amino acids) and positions 1074 to 1215 (142 amino acids) in the human PDS5A protein consisting of the amino acid sequence represented by SEQ ID NO: 2, when the initiator methionine is defined as position 1;

(b) polypeptides comprising one to several amino acid deletions, substitutions, and/or additions in the amino acid sequence of any one of the polypeptides (a).

In the present invention, the expression "consisting of an amino acid sequence" means that amino acid residues are arranged in a specific order. Therefore, for example, a "polypeptide consisting of the amino acid sequence represented by SEQ ID NO: 2" refers to a polypeptide which has the amino acid sequence of Met Asp Phe Thr . . . (omitted) . . . Asp Leu Gln Arg represented by SEQ ID NO: 2, and which has a size of 1337 amino acid residues. Further, in the present specification, the "polypeptide consisting of the amino acid sequence represented by SEQ ID NO: 2" is often abbreviated as the "polypeptide of SEQ ID NO: 2", for example. The same applies for the expression "consisting of a base sequence".

The term "immune-inducing activity" as used in the present invention refers to an ability to activate and propagate T cells that respond to cancer cells expressing the PDS5A protein. Specifically, the immune-inducing activity means that: the IFN-γ-producing ability of cytotoxic T cells and/or helper T cells stimulated by the PDS5A protein or a partial polypeptide thereof is higher than that of non-stimulated control T cells; the cytotoxic activity against cancer cells expressing the PDS5A protein of the cytotoxic T cells stimulated by the PDS5A protein or a partial polypeptide thereof is higher than that of the non-stimulated control T cells; the cytotoxic activity of the helper T cells stimulated by the PDS5A protein or a partial polypeptide thereof is enhanced, as compared to that of the non-stimulated control T cells; or the cytotoxic T cells or helper T cells stimulated by the PDS5A protein or a partial polypeptide thereof proliferate more than that of the non-stimulated control T cells.

The proliferation of cells can be confirmed by: visual observation; cell counting under a microscope; flow cytometry; the amount of tritium thymidine in the medium incorporated into the cells; and the like. Further, the measurement of the IFN-γ-producing ability can be performed, for example, by the known ELISPOT assay, and the like. Specifically, as will be described in the Examples below, for example, T cells are first cocultured with a polypeptide whose immune-inducing activity is to be evaluated (the PDS5A protein or a partial polypeptide thereof in the present invention) and antigen-presenting cells derived from peripheral blood mononuclear cells (hereinafter, referred to as "PBMCs"), to allow T cells to be contacted with the antigen-presenting cells presenting the polypeptide to be evaluated. Subsequently, the amount of IFN-γ produced by the T cells is measured using an antibody specific to IFN-γ. This allows for measuring the number of immune cells in the T cells. The immune-inducing activity can then be evaluated based on the thus obtained measurement results.

The cytotoxic activity can be evaluated, for example, by coculturing T cells with a polypeptide whose cytotoxic activity is to be evaluated (the PDS5A protein or a partial polypeptide thereof in the present invention) and antigen-presenting cells derived from PBMCs, and then analyzing whether or not the T cells show an ability to suppress the proliferation of tumor cells or to kill tumor cells (hereinafter, referred to as "cytotoxic activity") in vitro. The contact between the T cells and the antigen-presenting cells can be achieved by coculturing both of the cells in a liquid medium, as will be described later. The measurement of the cytotoxic activity can be carried out, for example, by a known method referred to as the $^{51}$Cr release assay, described in Int. J. Cancer, 58: P 317, 1994.

By administering the T cells induced as described above to a cancer-bearing living body, the size of tumor can be reduced or tumor can be regressed due to the cytotoxic activity of the T cells. Therefore, the above described immune-inducing activity can also be evaluated as an ability to suppress the proliferation of cancer cells, or as an ability to cause a reduction in size or the disappearance of a cancer tissue (tumor) (hereinafter, referred to as "anti-tumor activity").

In cases where the above described polypeptide is used for treatment or prevention of cancer, the evaluation of the immune-inducing activity is preferably carried out using the cytotoxic activity or the anti-tumor activity as an index, although the index is not particularly limited thereto.

Since a polypeptide of about 7 or more amino acid residues can include an epitope and such a polypeptide can exhibit antigenicity and immunogenicity, and can have an immune-inducing activity, as is well known in the art, and thus can be used as the immune inducer according to the present invention.

Accordingly, the polypeptide (a) is a polypeptide consisting of 7 or more consecutive amino acids, preferably 8, 9 or 10 or more consecutive amino acids, within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2; and having an immune-inducing activity. The polypeptide particularly preferably has the amino acid sequence of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2.

As a principle of immune induction by administration of a cancer antigen polypeptide, the polypeptide is incorporated into an antigen-presenting cell and then degraded into smaller fragments by peptidases in the cell, and subsequently, the fragments of the antigenic peptide are presented on the surface of the antigen-presenting cell. It is known that cytotoxic T cells and the like recognize antigens presented on the cell surface, and selectively kill cancer cells presenting the antigens on the cell surface. Further, it is also known that helper T cells recognize antigens presented on the surface of antigen-presenting cells, and enhance the induction of cytotoxic T cells that selectively kill cancer cells presenting the antigens on the on the cell surface. The size of the antigen polypeptide presented on the surface of the antigen-presenting cell is relatively small, and is about 7 to 30 amino acids. Therefore, in terms of allowing the polypeptide to be presented on antigen-presenting cells, the polypeptide (a) is preferably of about 7 to 30 consecutive amino acids, in the amino acid sequence of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2. A polypeptide consisting of about 8 to 30, about 9 to 30 or about 9 to 25 amino acids is sufficient. These relatively small polypeptides may be presented directly on the surface of the antigen-presenting cells without being incorporated into the cells.

Further, since the polypeptide incorporated into an antigen-presenting cell is cleaved at random sites by peptidases in the cell to yield various polypeptide fragments, and the resulting polypeptide fragments are then presented on the surface of the antigen-presenting cell, the administration of a large polypeptide, such as one having the amino acid sequence of positions 24 to 97, positions 113 to 132, positions 134 to 197, positions 204 to 225, positions 265 to 332, position 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2, inevitably leads to the production of polypeptide fragments active for immune induction via antigen-presenting cells, due to the degradation of the polypeptide in the antigen-presenting cells. Therefore, a large polypeptide can also be used for immunity induction via antigen-presenting cells. For example, a polypeptide consisting of 30 or more amino acids, preferably 40 or more, more preferably 50 or more, and still more preferably 100 or more amino acids may be used.

Further, the polypeptides according to the present invention can be checked with a checking medium, such as HLA Peptide Binding Predictions (bimas.dcrt.nih.gov/molbio/hla_bind/index.htmL) in Bioinformatics & Molecular Analysis Selection (BIMAS), or SYFPEITHI, which can search epitope peptides consisting of from 8 to 25, preferably from 9 to 24, and more preferably from 9 to 23 amino acids and having binding motifs for class I molecules or class II molecules of MHC (HLA, in humans) to be described later, to carry out the screening of peptides which may be epitope peptides. Specifically, the above described polypeptide is a polypeptide consisting of 7 or more consecutive amino acids within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2. Examples of the polypeptide include: polypeptides represented by SEQ ID NOs: 3 to 67; and polypeptides each comprising as a partial sequence any one of the polypeptides consisting of the amino acid sequences represented by SEQ ID NOs: 3 to 67, and having 10 to 30 amino acid residues. Among the polypeptides represented by SEQ ID NOs: 3 to 67, and the polypeptides each comprising as a partial sequence any one of the polypeptides consisting of the amino acid sequences represented by SEQ ID NOs: 3 to 67 and having 10 to 30 amino acid residues, the immune-inducing activity of the polypeptides represented by SEQ ID NOs: 3 to 67 is due to the binding to MHC class I molecules, and the immune-inducing activity of the polypeptides represented by SEQ ID NOs: 35 to 67 is due to the binding to MHC class II molecules.

On the other hand, the polypeptide (b) is a polypeptide comprising one or several amino acid substitutions, deletions and/or additions in the amino acid sequence of the polypeptide (a), and which has an immune-inducing activity. For example, the polypeptide (b) include a polypeptide comprising one or several amino acid substitutions, deletions and/or additions in the amino acid sequence represented by any one of SEQ ID NOs: 3 to 67.

The term "several" as used in the present invention refers to an integer of from 2 to 10, preferably an integer of from 2 to 6, more preferably an integer of 2 to 4, and still more preferably an integer of 2 or 3.

In general, it is thought that the modification of one or several amino acids in a polypeptide does not affect the functions of the original polypeptide; in some cases, such a modification is thought to even enhance a desired function of the original polypeptide. In fact, a modified peptide comprising one to several modifications (namely, substituted, deleted, added and/or inserted) in the amino acid sequence of the original amino acid sequence is known to retain the biological activity of the original peptide (Mark et al., 1984, Proc Natl Acad Sci USA, 81: 5662-5666, Zoller and Smith, 1982, Nucleic Acids Res. 10: 6487-6500, Dalbadie-McFarland et al., 1982, Proc Natl Acad Sci USA. 79: 6409-6413). Accordingly, the polypeptide (b) also may exhibit an immune-inducing activity, and thus may be used for the preparation of the immune inducer according to the present invention.

The 20 types of amino acids constituting naturally-occurring proteins can be classified into groups of amino acids with similar properties, such as, for example: neutral amino acids with side chains having low polarity (Gly, Ile, Val, Leu, Ala, Met and Pro); neutral amino acids having hydrophilic side chains (Asn, Gln, Thr, Ser, Tyr and Cys); acidic amino acids (Asp and Glu), basic amino acids (Arg, Lys and His); and aromatic amino acids (Phe, Tyr and Trp). It is known, in many cases, that the substitutions of amino acids within the same group do not alter the properties of the polypeptide. Therefore, in cases where an amino acid residue(s) in the polypeptide (a) of the present invention is/are substituted, the substitution(s) is/are preferably carried out within the same group, because it increases the likelihood of retaining the immune-inducing activity.

Further, the polypeptide (b) may be a polypeptide which has a sequence identity of 90% or more, preferably 95% or more, more preferably 98% or more, and still more preferably 99% or more or 99.5% or more to the amino acid sequence of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2, and which has an immune-inducing activity.

As used herein, the term "sequence identity" between amino acid sequences (or base sequences) refers to a percent value obtained by: aligning two amino acid sequences (or base sequences) to be compared such that the number of matched amino acid residues (or bases) between the amino acid sequences (or base sequences) is maximized; and dividing the number of matched amino acid residues (or the number of matched bases) by the total number of amino acid residues (or the total number of bases). When aligning sequences, a gap(s) is/are inserted into one or both of the two sequences to be compared, if required. Such alignment of sequences can be carried out using a known program such as BLAST, FASTA or CLUSTAL W. In cases where a gap(s) is/are inserted, the above-described total number of amino acid residues is the number of residues obtained by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

When used in connection with treatment or prevention of cancer, the polypeptide according to the present invention should be expressed on the surface of a cell or an exosome, preferably as a complex of the peptide and any of various classes of HLA. Accordingly, it is preferred to select a peptide having not only an immune-inducing activity, but also a high binding affinity to various classes of HLA. For this purpose, the peptide may be modified by substitution, insertion, deletion and/or addition of its amino acid residue(s), to obtain a modified peptide having an improved binding affinity. Since the regularity of the sequences of the peptides presented via binding to various classes of HLA is known, in addition to the regularity of naturally presented peptides (J Immunol, 1994, 152: 3913; Immunogenetics, 1995, 41: 178; J Immunol, 1994, 155: 4307), it is possible to introduce a modification based on such a regularity into the immunogenic peptide according to the present invention. For example, the substitution of the second amino acid from the N terminus with leucine or methionine, and/or the substitution of the amino acid at the C terminus with valine or leucine may be desirable for the purpose of improving the binding affinity to HLA-A24. Accordingly, a peptide having the amino acid sequence of any one of SEQ ID NOs: 20 to 34, in which the second amino acid from the N terminus is substituted with leucine or methionine, and/or the amino acid at the C terminus is substituted with valine or leucine, is also within the scope of the present invention.

Substitutions can be introduced not only at the terminal amino acids, but also at potential TCR recognition site(s) of peptides. Several studies have demonstrated that an amino acid-substituted peptide has the same or better properties as compared to the original peptide, and examples of the amino acid-substituted peptide include CAP1, p53 (264-272), Her-2/neu (369-377) and gp100 (209-217) (Zaremba et al. 1997, Cancer Res. 57: 4570-4577, T. K. Hoffmann et al. 2002, J Immunol. 168 (3): 1338-47, S. O. Dionne et al. 2003, Cancer Immunol immunother. 52: 199-206, and S. O. Dionne et al. 2004, Cancer Immunology, Immunotherapy, 53: 307-314).

In addition to the above described modifications, it is also possible to link the polypeptide according to the present invention with another substance(s), as long as the resulting linked polypeptide retains the necessary immune-inducing activity of the original peptide. Examples of the other substance include but not limited to peptides, lipids, sugars and sugar chains, acetyl groups, and natural and synthetic polymers. The peptide can also include a modification such as glycosylation, side-chain oxidation or phosphorylation, provided that the biological activity of the original peptide is not impaired due to the modification. These types of modifications can be carried out to confer additional functions (such as targeting function and delivery function) to the polypeptide, or to stabilize the polypeptide. For example, it is known in the art to introduce a D-amino acid, an amino acid mimic or a non-natural amino acid into a polypeptide in order to enhance the in vivo stability thereof; and this concept can be utilized in the polypeptides according to the present invention. The stability of a polypeptide can be assayed by several methods. For example, the stability can be tested using peptidases as well as various types of biological media such as human plasma and serum (see, for example, Verhoef et al., 1986, Eur J Drug Metab Pharmacokin, 11: 291-302).

Further, the polypeptide according to the present invention may be linked to another peptide(s) via a spacer(s) or a linker(s). Examples of the other peptide include but not limited to epitope peptides derived from other polypeptides. Alternatively, two or more polypeptides according to the present invention may be liked via a spacer(s) or a linker(s). The peptides to be linked via a spacer(s) or a linker(s) may be the same, or different from each other. The types of the spacer and the linker are not particularly limited, and examples thereof include those composed of peptides, more preferably, those composed of peptides having one or more cleavage sites that can be cleaved by enzymes such as peptidases, proteases and proteasomes. The linker or spacer may be, for example, AAY (P. M. Daftarian et al., J Trans Med, 2007, 5:26), AAA, NKRK (SEQ ID NO: 86) (R. P. M. Sutmuller et al., J Immunol. 2000, 165: 7308-7315), or one to several lysine residues (S. Ota et al., 2002, Can Res. 62: 1471-1476, K. S. Kawamura et al., 2002, J Immunol. 168: 5709-5715), but not limited thereto. The present invention contemplates a polypeptide linked to another peptide(s) via a spacer(s) or a linker(s).

In cases where the polypeptides according to the present invention contain cysteine residues, these polypeptides tend to form dimers via disulfide bonds between the SH groups of the cysteine residues. Therefore, the dimers of these polypeptides are also included in the polypeptides according to the present invention.

The polypeptides according to the present invention can be prepared using known techniques. For example, the polypeptides can be synthesized by a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers.

In addition, the polypeptide of interest may be obtained using known genetic engineering techniques, by: preparing a polynucleotide encoding the above polypeptide; incorporating the polynucleotide into an expression vector; introducing the vector into a host cell; and then allowing the polypeptide of interest to be produced in the host cell. When obtaining the polypeptide of interest from the host cells, the polypeptide can be purified or isolated such that the polypeptide does not substantially include other naturally-occurring host cell proteins and fragments thereof, or other arbitrary chemical substances.

The polynucleotide encoding the above polypeptide can be easily prepared by a known genetic engineering technique or a conventional method using a commercially available nucleic acid synthesizer. For example, DNA having the base sequence of SEQ ID NO: 1 can be prepared by carrying out PCR using a human chromosomal DNA or cDNA library as a template, and a pair of primers designed to amplify the base sequence represented by SEQ ID NO: 1. The reaction conditions for the PCR can be set as appropriate, and examples thereof include but not limited to repeating a cycle consisting of reactions at: 94° C. for 30 seconds (denaturation), 55° C. for 30 seconds to 1 minute (annealing) and 72° C. for 2 minutes (extension), for 30cycles, followed by a reaction at 72° C. for 1 minute. Further, the desired DNA can be isolated by preparing an appropriate probe(s) or primer(s) based on the information of the base sequence represented by SEQ ID NO: 1 and the amino acid sequence, and screening a cDNA library of human or the like using the probe(s) or primer(s). The cDNA library is preferably prepared from a cell, organ or tissue expressing the protein of SEQ ID NO: 2. The above described operations such as preparation of a probe(s) or primer(s), construction of a cDNA library, screening of a cDNA library and cloning of a gene of interest are known to those skilled in the art, and can be carried out according to the methods described, for example, in in Green, M. R. and Sambrook, J., 2012, Molecular Cloning: A Laboratory Manual Fourth Ed., Cold Spring Harbor Laboratory Press, Cold Spring Harbor, N.Y.; Current Protocolin Molecular Biology: www.currentprotocols.com; and the like. From the thus obtained DNA, DNA encoding the polypeptide (a) can be obtained. Further, since the codons encoding each amino acid are known, the base sequence of a polynucleotide encoding a specific amino acid sequence can be easily specified. Accordingly, the base sequence of a polynucleotide encoding the above described polypeptide (b) can also be easily specified, and thus, such a polynucleotide can also be synthesized using a commercially available nucleic acid synthesizer according to a conventional method.

The host cell may be any cell as long as it can express the above described polypeptide. Examples of prokaryotic cells include but not limited to *E. coli*; and Examples of eukaryotic cells include but not limited to mammalian cultured cells including monkey kidney cells COS-1 and Chinese hamster ovary cells CHO; budding yeast; fission yeast; silkworm cells; and *Xenopus laevis* egg cells.

In cases where a prokaryotic cell is used as the host cell, an expression vector containing an origin that enables its replication in a prokaryotic cell, a promoter, a ribosome binding site, a DNA cloning site a terminator, etc. is used. Examples of the expression vector for *E. coli* include the pUC system, pBluescript II, pET expression system and pGEX expression system. The polypeptide encoded by the DNA can be expressed in the prokaryotic host cell by incorporating a DNA encoding the above polypeptide into such an expression vector, transforming a prokaryotic host cell with such a vector, and then culturing the resulting transformant. In this process, the polypeptide can also be expressed as a fusion protein with another protein.

In cases where a eukaryotic cell is used as the host cell, an expression vector for eukaryotic cells containing a promoter, a splicing site, poly(A) addition site, etc. is used. Examples of such an expression vector include pKA1, pCDM8, pSVK3, pMSG, pSVL, pBK-CMV, pBK-RSV, EBV vector, pRS, pcDNA3, pMSG and pYES2. In the same manner as described above, the polypeptide encoded by the DNA can be expressed in the eukaryotic host cell by incorporating a DNA encoding the above polypeptide into such an expression vector, transforming a eukaryotic host cell with such a vector, and then culturing the resulting transformant. In cases where pINDN5-His, pFLAG-CMV-2, pEGFP-N1, pEGFP-C1 or the like is used as the expression vector, the above polypeptide can be expressed as a fusion protein to which any of various types of tags, such as His tag, FLAG tag, myc tag, HA tag and GFP, is added.

The introduction of the expression vector into the host cell can be carried out by a known method such as electroporation, the calcium phosphate method, the liposome method or the DEAE dextran method.

The polypeptide of interest can be isolated and purified from the host cells by a combination of known separation operations. Examples of the known separation operations include but not limited to: treatment with a denaturant such as urea or with a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those in the form of a fusion protein with another arbitrary protein. Examples thereof include fusion proteins with glutathione S-transferase (GST) and fusion proteins with a His tag. Accordingly, such a polypeptide in the form of a fusion protein is also included within the scope of the present invention. Further, a polypeptide expressed in the transformed cell may be modified post-translationally in various ways. Such a post-translationally modified polypeptide is also included within the scope of the present invention, as long as it has an immune-inducing activity. Examples of such a post-translational modification include: elimination of N-terminal methionine; N-terminal acetylation; glycosylation; limited degradation by an intracellular protease; myristoylation; isoprenylation and phosphorylation.

<Immune Inducer>

An already existing tumor can be regressed by administering the polypeptide having an immune-inducing activity according to the present invention, or an expression vector containing the gene encoding the polypeptide, to a cancer-bearing living body. Further, the occurrence of a tumor can be prevented by administering the above described polypeptide having an immune-inducing activity or the gene encoding the polypeptide to a living body before the onset of cancer. Accordingly, the polypeptide according to the present invention or the gene encoding the polypeptide may be used as an active ingredient in immune inducer.

The terms "tumor" and "cancer" are each used herein to refer to a malignant neoplasia, and are used interchangeably. In this case, the cancer to be treated is preferably a cancer expressing the PDS5A protein, and more preferably leukemia, malignant lymphoma, prostate cancer, liver cancer, breast cancer, pancreatic cancer, ovarian cancer, renal cancer, colorectal cancer, stomach cancer, malignant brain tumor, lung cancer or esophageal cancer.

The subject animal is preferably a mammal, more preferably a mammal such as a primate, a pet animal, a domestic animal or a sport animal, still more preferably a human, a dog or a cat, and particularly preferably a human.

The cancer-affected individual (a cancer patient, in cases where the individual is a human) to be treated is preferably a cancer-affected individual whose cancer cells express the PDS5A protein in vivo. Specifically, preferred is a cancer-affected individual screened by the method of detecting cancer described in WO 2011/027807. In particular, the cancer-affected individual is preferably one screened by the fact that the expression levels of antibodies against the PDS5A protein contained in the sample obtained from the subject living body are higher as compared to the expression levels of the antibodies contained the sample obtained from a healthy individual. Examples of the sample to be used for screening of cancer-affected individuals to be treated include bodily fluids such as blood, serum, plasma, ascites and pleural effusion; tissues; and cells. In cases where the screening is carried out by measuring the expression levels of antibodies against the PDS5A protein, the sample is preferably serum, plasma, ascites or pleural effusion.

The administration of the immune inducer according to the present invention may be carried out either orally or parenterally. However, preferred administration routes are parenteral administrations such as intramuscular administration, subcutaneous administration, intravenous administration and intraarterial administration. In cases where the immune inducer is used for treatment of cancer, it can be administered to a regional lymph node in the vicinity of the tumor to be treated, in order to enhance its anti-cancer activity. The immune inducer can be administered in any dosage amount effective for inducing immunity. For example, in cases where the immune inducer is used for treatment or prevention of cancer, the agent may be administered in an amount effective for treatment or prevention of cancer. The amount effective for treatment or prevention of cancer can be selected as appropriate depending on the size of the tumor, symptoms, body weight and volume of the subject animal, and the like. In cases where the subject animal is a human, the effective amount is usually from 0.0001 to 1,000 µg, and preferably from 0.001 to 1,000 µg per day. The above described dosage amount can be administered in a single dose, or in several divided doses. It is preferred that the above dosage amount be divided and administered several times per day, and that the administration thereof be carried out every several days or several months. As will be specifically described in the Examples below, the immune inducer according to the present invention can regress an already formed tumor. Thus, since the immune inducer can exert its anti-cancer activity also against a small number of cancer cells in the early stages, the development or recurrence of cancer can be prevented by using the agent before the onset or after the treatment of the cancer. In other words, the immune inducer according to the present invention is useful in both the treatment and prevention of cancer, and can be used as an active ingredient in an agent for treating or preventing cancer.

The immune inducer according to the present invention contains as an active ingredient the above described polypeptide according to the present invention, and may consist of a single polypeptide, or of a combination of a plurality of polypeptides. By combining a plurality of the polypeptides according to the present invention, the immunity-inducing activity (activity to induce and activate cytotoxic T cells) of each of the polypeptides is enhanced, and a more efficient treatment or prevention of cancer may be achieved.

The immune inducer according to the present invention can also be used in combination with a known peptide(s) capable of inducing cytotoxic T cells. By combining the polypeptide(s) according to the present invention with such a known peptide(s), the immunity-inducing activity (activity to induce and activate cytotoxic T cells) of each of the polypeptides is enhanced, and a more efficient treatment or prevention of cancer may be achieved. The term "combination" as used in this case includes the case in which the immune inducer according to the present invention and a known peptide(s) capable of inducing cytotoxic T cells are administered separately or simultaneously. The expression "to be administered separately" as used herein means that the immune inducer according to the present invention and a known peptide(s) capable of inducing cytotoxic T cells are administered separately at different time points with a certain time interval therebetween. The order of administration is not limited. On the other hand, the expression "to be administered simultaneously" means that the immune inducer according to the present invention and a known peptide(s) capable of inducing cytotoxic T cells are mixed in advance and administered in the form of a mixture, or that the immune inducer according to the present invention and a known peptide(s) capable of inducing cytotoxic T cells are administered in separate forms but at the same time without any time interval.

The immune inducer according to the present invention can be used in combination with another immunopotentiator capable of enhancing the immune response in vivo. The other immunopotentiator may be included in the immune inducer according to the present invention, or may be administered to a patient as a separate composition, in combination with the administration of the immune inducer according to the present invention.

The "other immunopotentiator" includes, for example, an adjuvant. An adjuvant can enhance the immune response by providing an antigen reservoir (extracellularly or within macrophages), activate macrophages and stimulate specific sets of lymphocytes, so as to enhance the anti-cancer activity. Therefore, in cases where the immune inducer according to the present invention is used as an active ingredient in an agent for treating or preventing cancer, it is preferred that the immune inducer further contain an adjuvant, in addition to the polypeptide according to the present invention as an active ingredient. Many types of adjuvants are known in the art, and any of these adjuvants can be used. Specific examples of the adjuvants include MPL (SmithKline Beecham), analogs of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in PCT application WO 96/33739 (SmithKline Beecham); QS-7, QS-17, QS-18 and QS-L1 (So, H. S., et al., "Molecules and cells", 1997, 7: 178-186); Freund's incomplete adjuvant; Freund's complete adjuvant; vitamin E; Montanide; alum; CpG oligonucleotides (see, for example, Kreig, A. M., et al., 1995, Nature 374: 546-549); poly-I:C and derivatives thereof (such as poly ICLC); and various water-in-oil emulsions prepared from biodegradable oils such as squalene and/or tocopherol. Among these, Freund's incomplete adjuvant; Montanide; poly-I:C and derivatives thereof; and CpG oligonucleotides are preferred. The mixing ratio of the above-described adjuvant to the polypeptide is typically from about 1:10 to 10:1, preferably from about 1:5 to 5:1, and more preferably about 1:1. However, the adjuvant is not limited to the above-described examples, and any adjuvant known in the art other than those described above can also be used, when administering the immune inducer according to the present invention (see, for example, Goding, "Monoclonal Antibodies: Principles and Practice", 2nd edition, 1986). Methods for preparing a mixture or an emulsion of an immune inducer and an adjuvant are well-known to those skilled in the art of vaccination.

Further, in addition to the above-described adjuvants, factors that stimulate the immune response of the subject may be used as the other immunopotentiator. For example, any of various types of cytokines having a property to stimulate lymphocytes and/or antigen-presenting cells can be used as the immunopotentiator in combination with the immune inducer according to the present invention. A number of such cytokines capable of enhancing the immune response are known to those skilled in the art, and examples thereof include but not limited to interleukin-12 (IL-12), GM-CSF, IL-18, interferon-α (IFN-α), interferon-β (IFN-β), interferon-ω (IFN-ω), interferon-γ (IFN-γ), and Flt3 ligand, which have been shown to enhance the protective action of vaccines. Any of such factors can also be used as the above-described immunopotentiator, and can be administered to a patient in combination with the immune inducer according to the present invention, either by being incorporated into the immune inducer according to the present invention, or as a separate composition.

<Agent for Treating or Preventing Cancer>

The immune inducer according to the present invention can be used as an active ingredient in an agent for treating or preventing cancer.

The agent for treating or preventing cancer can be formulated by mixing, as appropriate, the immune inducer according to the present invention with an additive(s) such as a pharmaceutically acceptable carrier, diluent and/or excipient suitable for each dosage form.

Formulation methods and additives which can be used are well-known in the art of pharmaceutical formulation, and any of the methods and additives can be used. Specific examples of the additives include but not limited to: diluents such as physiological buffer solutions; excipients such as sugar, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the dosage form include oral preparations such as tablets, capsules, granules, powders and syrups; and parenteral preparations such as inhalants, injection solutions, suppositories and solutions. These formulations can be prepared by commonly known production methods.

<Antigen-Presenting Cells>

The polypeptide can be presented by the antigen-presenting cells by bringing the above described polypeptide into contact with antigen-presenting cells in vitro. In other words, the above described polypeptide (a) or (b) can be used as an agent for treating antigen-presenting cells. As the antigen-presenting cells, dendritic cells or B cells having MHC class I molecules and class II molecules can be preferably used. A variety of MHC class I molecules and class II molecules have been identified and are well known. MHC molecules in humans are referred to as HLA.

Examples of HLA class I molecules include HLA-A, HLA-B and HLA-C. More specific examples of HLA class I molecules include HLA-A, HLA-B and HLA-C; and still more specific examples thereof include HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

Examples of HLA class II molecules include HLA-DR, HLA-DQ and HLA-DP; and more specific examples thereof include HLA-DRB1*01, HLA-DRB1*03, HLA-DRB1*04, HLA-DRB1*0405, HLA-DRB1*07, HLA-DRB1*08, HLA-DRB1*11, HLA-DRB1*13, HLA-DRB1*15, HLA-DRB1*15, HLA-DQA1, HLA-DQB1 and HLA-DPB1.

The dendritic cells or B cells having HLA class I or HLA class II molecules can be prepared from blood or the like by a well-known method. For example, tumor specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

An immune response desirable for treating cancer may be induced by administering an effective amount of the thus obtained dendritic cells. The cells to be used can be obtained from bone marrow or umbilical cord blood provided by a healthy individual, or bone marrow or peripheral blood or the like of the patient himself. The use of autologous cells obtained from the patient himself is preferred, because they are highly safe and serious side effects are expected to be avoided. The peripheral blood or bone marrow may be any of a fresh sample, a cold-stored sample and a frozen sample. The peripheral blood may be obtained by culturing whole blood, or by culturing separated leukocyte components alone, and the latter is more efficient and thus preferred. Further, mononuclear cells may be separated among the leukocyte components. In cases where the cells to be used are those derived from bone marrow or umbilical cord blood, all the cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are derived, as well as CD4-positive cells and the like. There is no particular limitation on the method for producing the cytokines to be used, and any cytokine, either natural or recombinant, can be used as long as its safety and physiological activity have been confirmed. It is preferred to use a preparation with assured quality for medical use, in a minimum amount necessary. The concentration of the cytokine(s) to be added is not particularly limited as long as it can induce dendritic cells. In general, the total concentration of the cytokine(s) is preferably from about 10 to 1,000 ng/mL, and more preferably from about 20 to 500 ng/mL. The culture can be carried out using a well-known medium commonly used for culturing leukocytes. The temperature for cultivation is not particularly limited as long as it can propagate the leukocytes; however a temperature of about 37° C., which is the human body temperature, is most preferred. Further, the atmospheric environment during the culture is not particularly limited as long as it can propagate the leukocytes; however it is preferred that 5% $CO_2$ is allowed to flow. The period of time for cultivation is not particularly limited as long as a required number of cells can be induced within the period. The culture is usually carried out for a period of from 3 days to 2 weeks. The apparatuses used for separation and culture of the cells can be selected as appropriate. Preferred are apparatuses whose safety for medical use has been confirmed, and which can be operated stably and simply. As for the cell culturing apparatus, in particular, it is possible to use, not only a common vessel such as a Petri dish, flask or bottle, but also a multi-layer vessel, a multi-stage vessel, a roller bottle, a spinner bottle, a bag-type culture vessel, a hollow fiber column or the like.

The process for bringing the above-described polypeptide into contact with the antigen-presenting cells in vitro can be carried out by a well-known method. For example, it can be achieved by culturing the antigen-presenting cells in a culture medium containing the above described polypeptide. The concentration of the peptide in the medium is not particularly limited, and it is usually from about 1 to 100 μg/mL, and preferably from about 5 to 20 μg/mL. The cell density during the culture is not particularly limited, and it is usually from about $10^3$ to $10^7$ cells/mL, and preferably from about $5\times10^4$ to $5\times10^6$ cells/mL. The culture is preferably carried out at 37° C. under an atmosphere of 5% $CO_2$, according to a conventional method. The maximum length of the peptide which can be presented on the surface of the antigen-presenting cells is usually a length of about 30 amino acid residues. Therefore, in cases where the antigen-presenting cells are brought into contact with the polypeptide in vitro, the polypeptide may be prepared such that its length is not more than about 30 amino acid residues, but not particularly limited thereto.

By culturing the antigen-presenting cells with the above described polypeptide, the polypeptide is incorporated into MHC molecules of the antigen-presenting cells, and presented on the surface of the antigen-presenting cells. Thus, isolated antigen-presenting cells containing the complex of the polypeptide and the MHC molecule may be prepared using the above described polypeptide. Such antigen-presenting cells can present the polypeptide to T cells in vivo or in vitro, induce cytotoxic T cells or helper T cells specific to the polypeptide, and propagate these cells.

By bringing the thus prepared antigen-presenting cells containing the complex of the above described polypeptide and the MHC molecule, into contact with T cells, in vitro, it is possible to induce cytotoxic T cells or helper T cells specific to the polypeptide, and to allow the proliferation of these cells. This can be achieved by coculturing the antigen-presenting cells and T cells in a liquid medium. For example, it can be carried out by suspending the antigen-presenting cells in a liquid medium, placing the resulting suspension in a vessel, such as in wells of a microplate, adding T cells thereto, and then culturing the cells. The mixing ratio of the antigen-presenting cells to the T cells when coculturing these cells is not particularly limited, and is usually from about 1:1 to 1:100, and preferably from about 1:5 to 1:20 in terms of the number of the cells. The density of the antigen-presenting cells to be suspended in the liquid medium is not particularly limited, and it is usually from about 100 to 10 million cells/ml, and preferably from about 10,000 to 1 million cells/ml. Coculture is preferably carried out at 37° C. under an atmosphere of 5% $CO_2$, according to a conventional method. The period of time for culturing is not particularly limited, and it is usually from about 2 days to 3 weeks, and preferably from about 4 days to 2 weeks. Further, coculture is preferably carried out in the presence of one or more types of interleukins such as IL-2, IL-6, IL-7 and/or IL-12. In such cases, the concentration of IL-2 or IL-7 is usually from about 5 to 20 U/mL, the concentration of IL-6 is usually from about 500 to 2000 U/mL, and the concentration of IL-12 is usually from about 5 to 20 ng/mL, but not limited thereto. The above described coculture may be repeated once or several times, adding fresh antigen-presenting cells. For example, the operation of discarding the culture supernatant after the coculture and adding a fresh suspension of the antigen-presenting cells to further carrying out the coculture, may be repeated once or several times. The conditions for each coculture may be the same as described above.

The above described coculture allows for the induction and proliferation of cytotoxic T cells and helper T cells specific to the polypeptide. Thus, isolated T cells which selectively bind to the complex of the polypeptide and the MHC molecule may be prepared with the use of the above described polypeptide.

As will be described in the Examples below, the gene (PDS5A gene) encoding the PDS5A protein is expressed specifically in each of: leukemia leukocytes, malignant lymphoma tissues, malignant lymphoma cells, prostate cancer tissues, prostate cancer cells, liver cancer tissues, liver cancer cells, breast cancer tissues, breast cancer cells, pancreatic cancer tissues, pancreatic cancer cells, ovarian cancer tissues, ovarian cancer cells, renal cancer tissues, renal cancer cells, colorectal cancer tissues, colorectal cancer cells, stomach cancer tissues, stomach cancer cells, malignant brain tumor tissues, malignant brain tumor cells, lung cancer tissues, lung cancer cells, esophageal cancer tissues and esophageal cancer cells. Therefore, a significantly higher amount of the PDS5A protein is thought to be present in the cells of these cancer types, than in normal cells. When cytotoxic T cells or helper T cells prepared as described above are administered to a living body, while a part of the PDS5A protein present in cancer cells is presented by MHC molecules on the surface of the cancer cells, the thus presented protein serves as a marker to allow the cytotoxic T cells to damage the cancer cells, or enhance the cytotoxic activity of the cytotoxic T cells. Since antigen-presenting cells presenting the above described polypeptide can induce, and propagate cytotoxic T cells and helper T cells specific to the polypeptide, also in vivo, the administration of the antigen-presenting cells to a living body can also allow the cytotoxic T cells to damage the cancer cells, or enhance the cytotoxic activity of the cytotoxic T cells. In other words, the cytotoxic T cells and helper T cells as well as the antigen-presenting cells prepared using the above polypeptide are also useful as agents for treating or preventing cancer, as is the immune inducer according to the present invention.

In the case of administering the above described isolated antigen-presenting cells or isolated T cells to a living body, these cells are preferably prepared by treating antigen-presenting cells or T cells collected from the patient to be treated, with the polypeptide (a) or (b) as described above, in order to avoid the immune response in the living body, that attacks these cells as foreign substances.

The agent for treating or preventing cancer comprising as an active ingredient the antigen-presenting cells or isolated T cells is preferably administered via a parenteral administration route such as intravenous or intraarterial administration. The dosage amount is selected as appropriate depending on the symptoms, the purpose of administration and the like. The dosage amount is usually from one to 10 trillion cells, and preferably from 1 million to 1 billion cells, which amount is preferably administered once in several days or several months. The formulation may be, for example a suspension of the cells in physiological buffered saline, and the formulation may be used in combination with another anti-cancer agent(s), cytokine(s) and/or the like. Further, one, or two or more additives known in the field of pharmaceutical formulation can also be added to the formulation.

<Gene Vaccine>

Immune induction, namely, the induction of antibody production or cytotoxic T cells in the body of a subject animal, can also be achieved by allowing a polynucleotide encoding the polypeptide (a) or (b) to be expressed in the living body. This provides an effect equivalent to that provided by administering the polypeptide. In other words, the immune inducer according to the present invention may comprise as an active ingredient a recombinant vector which contains the polynucleotide encoding the above described polypeptide (a) or (b) and which can express the polypeptide in a living body. Such a recombinant vector capable of expressing an antigen polypeptide, which will be shown in the Examples below, is also referred to as a "gene vaccine".

The vector to be used for the production of a gene vaccine is not particularly limited as long as it can express a polypeptide in a cell of the subject animal (preferably, in a mammalian cell). The vector may be either a plasmid vector or a virus vector, and any vector known in the field of gene vaccines may be used. The polynucleotide, such as DNA or RNA, encoding the above described polypeptide can be easily prepared as described above, by a conventional method. Further, the polynucleotide may be incorporated into a vector using a method well-known to those skilled in the art.

The gene vaccine is preferably administered by a parenteral administration route, such as intramuscular, subcutaneous, intravenous or intraarterial administration. The dosage amount of the gene vaccine can be selected as appropriate depending on the type of the antigen and the like, and it is usually from about 0.1 µg to 100 mg, and preferably from about 1 µg to 10 mg, in terms of the weight of the gene vaccine per 1 kg of body weight.

The method utilizing a virus vector may be, for example, a method in which a polynucleotide encoding the above described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. In particular, a method utilizing a retrovirus, adenovirus, adeno-associated virus, vaccinia virus or the like is particularly preferred.

Examples of other methods include a method in which an expression plasmid is directly administered intramuscularly (DNA vaccine method), the liposome method, lipofectin method, microinjection method, calcium phosphate method and electroporation method. Of these, the DNA vaccine method and liposome method are particularly preferred.

Methods for allowing the gene encoding the polypeptide used in the present invention to actually act as a pharmaceutical include: an in vivo method comprising directly introducing the gene into the body of a subject; and an ex vivo method comprising collecting a certain type of cells from a subject animal, and introducing the gene into the cells ex vivo, followed by returning the cells to the body of the subject animal. Of these, the in vivo method is more preferred.

In cases where the gene is administered by the in vivo method, the gene may be administered through an appropriate administration route depending on the disease to be treated, symptoms and the like. For example, the gene can be administered by an intravenous, intraarterial, subcutaneous, intramuscular administration or the like. In the case of administering the gene by the in vivo method, the gene may be formulated into a dosage form such as a solution; but generally formulated as an injection solution or the like containing DNA encoding the above described peptide according to the present invention as an active ingredient. A commonly used carrier(s) may be added thereto if required. In the case of using a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence represented by SEQ ID NO:1" includes not only the base sequence actually represented by SEQ ID NO: 1, but also the sequence complementary thereto. Thus, "a polynucleotide having the base sequence represented by SEQ ID NO:1" includes a single-stranded polynucleotide having the base sequence actually represented by SEQ ID NO:1, a single-stranded polynucleotide having the base sequence complementary thereto, and a double-stranded polynucleotide consisting of these single-stranded polynucleotides. When the polynucleotide encoding the polypeptide used in the present invention is prepared, any one of these base sequences is to be selected as appropriate, which selection can be easily carried out by those skilled in the art.

EXAMPLES

The present invention will be more specifically described below, by way of Examples.

Example 1: Analysis of Expression in Various Tissues (1) Analysis of PDS5A Gene Expression in Various Cancer Cell Lines The gene sequence (SEQ ID NO: 1) encoding the amino acid sequence of human PDS5A protein is obtained from Gene Bank. The expression of the thus obtained gene in various types of human cell lines was analyzed by RT-PCR (Reverse Transcription-PCR). The reverse transcription reaction was carried out as follows. Specifically, from 50 to 100 mg of each tissue or 5 to 10×10$^6$ cells of each cell line, total RNA was extracted using TRIZOL reagent (manufactured by Life Technologies, Inc.) according to the protocol described in the attached instructions. The thus obtained total RNA was used to synthesize cDNA, using Superscript First-Strand Synthesis System for RT-PCR (manufactured by Life Technologies, Inc.) according to the protocol described in the attached instructions. As the cDNAs of normal human tissues (brain, hippocampus, testis, colon and placenta), Gene Pool cDNA (manufactured by Life Technologies, Inc.), QUICK-Clone cDNA (manufactured by Clontech Laboratories, Inc.) and Large-Insert cDNA Library (manufactured by Clontech Laboratories, Inc.) were used. The PCR reaction was carried out as follows, using primers specific to the obtained gene (the base sequences of the primes are represented by SEQ ID NOs: 68 and 69). Specifically, reagents and an attached buffer were added to prepare a mixture having a total volume of 25 µL, and containing 0.25 µL of a sample prepared by the reverse transcription reaction, 2 µM each of the above described primers, 0.2 mM each of dNTPs, and 0.65 U of ExTaq polymerase (manufactured by Takara Shuzo Co., Ltd.). The reaction was then carried out using Thermal Cycler (manufactured by Bio-Rad laboratories Inc.) by repeating a cycle consisting of reactions at 94° C. for 30 seconds, 55° C. for 30 seconds and 72° C. for 1 minute, for 30 times. At the same time, primers specific to GAPDH, which is a housekeeping gene (the base sequences of human GAPDH primers are represented by SEQ ID NOs: 70 and 71) were used as a control for comparison.

As a result, as shown in FIG. 1, the expression of the human PDS5A gene was detected in most of the cancer cell lines, namely, in the cell lines of leukemia, malignant lymphoma, prostate cancer, liver cancer, breast cancer, pancreatic cancer, ovarian cancer, renal cancer, colorectal cancer, stomach cancer, malignant brain tumor, lung cancer and esophageal cancer.

(2) Expression of PDS5A Protein in Human Cancer Tissue (Immunohistochemical Staining)

Immunohistochemical staining was carried out on 72 cancer tissue specimens in a paraffin-embedded multiple cancer tissue array (manufactured by Biomax Inc.). The human cancer tissue array was treated at 60° C. for 3 hours, and placed in a staining jar filled with xylene, and the operation of replacing xylene with a fresh one every 5 minutes was repeated 3 times. Subsequently, the same operation was carried out using ethanol and PBS-T instead of xylene. The human cancer tissue array was placed in a staining jar filled with a 10 mM citrate buffer solution (pH 6.0) containing 0.05% Tween 20, treated at 125° C. for 5 minutes, and then left to stand at room temperature for 40 minutes or more. Excess moisture around the tissue sections was wiped off with Kimwipes, the tissue sections were encircled using a DAKOPEN, and an adequate amount of Peroxidase Block (manufactured by DAKO) was added dropwise thereto. After allowing the array to stand at room temperature for 5 minutes, the array was placed in a staining jar filled with PBS-T, and the operation of replacing PBS-T with a fresh one every 5 minutes was repeated 3 times. A PBS-T solution containing 10% FBS, as a blocking solution, was applied to the array, and the array was left to stand in a moist chamber at room temperature for 1 hour. Subsequently, a commercially available rabbit polyclonal antibody (manufactured by Sigma-Aldrich Co. LLC.) which reacts to the PDS5A protein was diluted with a PBS-T solution containing 5% FBS to a concentration of 10 µg/mL, and the resulting solution was applied to the array, followed by allowing the array to stand overnight in a moist chamber controlled at 4° C. After washing the array with PBS-T for 10 minutes, for 3 times, an adequate amount of Peroxidase Labelled Polymer Conjugated (manufactured by DAKO) was added dropwise thereto, and the array was left to stand in a moist chamber at room temperature for 30 minutes. After washing the array with PBS-T for 10 minutes, for 3 times, a DAB color-developing solution (manufactured by DAKO) was applied thereto, and the array was left to stand at room temperature for about 10 minutes. Thereafter, the color-developing solution was discarded, and the array was washed with PBS-T for 10 minutes, for 3 times, followed by rinsing with distilled water. The array was then successively dipped in 70%, 80%, 90%, 95% and 100% ethanol solutions for 1 minute each, and then left to stand overnight immersed in xylene. The glass slide of the array was recovered, mounted with Glycergel Mounting Medium (manufactured by DAKO), and then observed.

As a result, strong expression of PDS5A protein was observed in most of the tissues of the cancers tested, namely: prostate cancer, liver cancer, breast cancer, pancreatic cancer, ovarian cancer, renal cancer, colorectal cancer, stomach cancer, malignant brain tumor, lung cancer and esophageal cancer.

Example 2: Induction of Peptide Epitope-Reactive CD8-Positive T Cells (1) Prediction of Peptide Motifs which Bind to HLA-A0201 and HLA-A24

Information on the amino acid sequence of the human PDS5A protein represented by SEQ ID NO: 2 was obtained from GenBank. For the prediction of HLA-A0201 and HLA-A24 binding motifs, the amino acid sequence of the human PDS5A protein was analyzed with a computer-based prediction program using a known BIMAS software (available at bimas.dcrt.nih.gov/molbio/hla_bind/). As a result, 17 types of polypeptides consisting of the amino acid sequences represented by SEQ ID NOs: 3 to 19, which were expected to be capable of binding to the HLA-A0201 molecule; and 14 types of polypeptides consisting of the amino acid sequences represented by SEQ ID NOs: 20 to 34, which were expected to be capable of binding to the HLA-A24 molecule; were selected. All the selected polypeptides were synthesized by Greiner Japan Co. Ltd. that provides custom peptide synthesis services. The quality of the synthesized polypeptides has been guaranteed by HPLC analysis and mass spectrometry.

(2) Induction of Peptide Epitope-Reactive CD8-Positive T Cells

Peripheral blood was separated from the blood of an HLA-A0201-positive healthy individual. The peripheral blood was layered on Lymphocyte separation medium (Organon Teknika Corporation, Durham, N.C.), and then centrifuged at 1,500 rpm at room temperature for 20 minutes. A PBMC-containing fraction was collected and washed 3 times (or more) with a cold phosphate buffer solution to obtain PBMCs. The thus obtained PBMCs were suspended in 20 mL of AIM-V medium (manufactured by Life Technologies, Inc.), and allowed to adhere to a culture flask (manufactured by Falcon Plastics Co.) for 2 hours under the conditions of 37° C. and 5% $CO_2$. Non-adherent cells were used for the preparation of T cells, and adherent cells were used for the preparation of dendritic cells.

The adherent cells were cultured in AIM-V medium in the presence of IL-4 (1,000 U/ml) and GM-CSF (1,000 U/ml). Six days later, the medium was replaced with AIM-V medium supplemented with IL-4 (1,000 U/mL), GM-CSF (1,000 U/mL), IL-6 (1,000 U/mL, manufactured by Genzyme Corporation), IL-1β (10 ng/mL, manufactured by Genzyme Corporation) and TNF-α (10 ng/mL, manufactured by Genzyme Corporation), and the cells were cultured for another 2 days. The resulting population of the non-adherent cells was used as the dendritic cells.

The thus prepared dendritic cells were suspended in AIM-V medium at a cell density of $1\times10^6$ cells/mL. Each of the peptides which were selected in the above described (1) and expected to be capable of binding to the HLA-A0201 molecule was added to the cells at a concentration of 10 µg/mL, followed by culturing for 4 hours under the conditions of 37° C. and 5% $CO_2$, using a 96-well plate. After the cultivation, the cells were irradiated with X-ray (3000 rad), washed with AIM-V medium, suspended in AIM-V medium containing 10% human AB serum (manufactured by Nabi Biopharmaceuticals Inc.), IL-6 (1,000 U/mL) and IL-12 (10 ng/mL, manufactured by Genzyme Corporation), and then placed in wells of a 24-well plate at a population of $1\times10^5$ cells per well. Further, the prepared T cell population was added to the wells at a population of $1\times10^6$ cells per well, and the cells were cultured under the conditions of 37° C. and 5% $CO_2$. Seven days later, each culture supernatant was discarded. Then, dendritic cells obtained in the same manner as described above by the treatment with each peptide and the subsequent X-ray irradiation were suspended (cell density: $1\times10^5$ cells/mL) in AIM-V medium containing 10% human AB serum (manufactured by Nabi Biopharmaceuticals Inc.), IL-7 (10 U/mL, manufactured by Genzyme Corporation) and IL-2 (10 U/mL, manufactured by Genzyme Corporation), and the resulting suspension was added to the wells of the 24-well plate at a population of $1\times10^5$ cells per well, followed by further culturing the cells. The same procedures were repeated 4 times at intervals of 7 days, and the stimulated T cells were then collected. Thereafter, the induction of CD8-positive T cells was confirmed by flow cytometry.

Further, the same treatment as described above was carried out, using as a negative control, a peptide (SEQ ID NO: 74) having a sequence outside the scope of the present invention; and using as Comparative Examples, known peptides (SEQ ID NOs: 75 to 83) which bind to the HLA-A0201 molecule, and the PDS5A protein which had been prepared according to Example 5 in WO 2011/027807 and which consists of the amino acid sequence represented by SEQ ID NO: 2.

The induction of peptide epitope-reactive CD8-positive T cells was attempted also for the peptides expected to be capable of binding to the HLA-A24 molecule, in the same manner as described above, using dendritic cells and a T cell population induced from peripheral blood of an HLA-A24-positive healthy individual. Further, the same treatment as described above was carried out, using as a negative control, a peptide (SEQ ID NO: 84) having a sequence outside the scope of the present invention; and using as a Comparative Example, the PDS5A protein consisting of the amino acid sequence represented by SEQ ID NO: 2.

Example 3: Determination of Cytotoxic T Cell Antigen Epitopes (1) IFN-γ-Producing Ability In order to examine the specificity of the respective T cells induced in Example 2 (2), to the respective epitope peptides and the protein, dendritic cells expressing the HLA-A0201 molecule were pulsed with various types of polypeptides. The dendritic cells were prepared by culturing in AIM-V medium supplemented with each polypeptide at a concentration of 10 µg/mL under the conditions of 37° C. and 5% $CO_2$ for 4 hours. As the various types of polypeptides, the respective polypeptides represented by the amino acid sequences of SEQ ID NOs: 3 to 19 and expected to be capable of binding to the HLA-A0201 molecule, the negative control polypeptide (SEQ ID NO: 74), the known polypeptides (SEQ ID NOs: 75 to 83) which bind to the HLA-A0201 molecule, and the PDS5A protein consisting of the amino acid sequence represented by SEQ ID NO: 2, were used. To 5×10⁴ dendritic cells which had been pulsed with each peptide, 5×10³ T cells were added, and the cells were cultured for 24 hours in AIM-V medium containing 10% human AB serum, in a 96-well plate. Each supernatant after the cultivation was collected, and the amount of IFN-γ produced was measured by ELISA.

Figure 2:
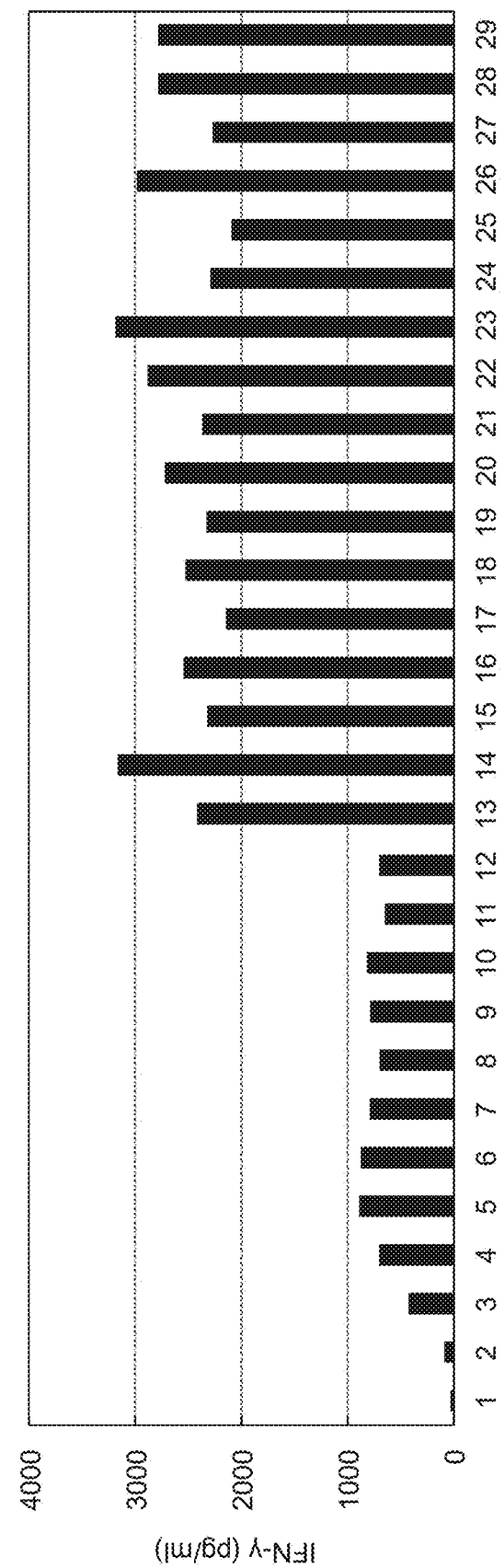
FIG. 2 shows that CD8-positive T cells specific to each of polypeptides consisting of the amino acid sequences represented by SEQ ID NOs: 3 to 19 recognize the complex consisting of the polypeptide and HLA-A0201 and produce IFN-γ.

As a result, a clearly higher IFN-γ production was observed in the supernatants of Lanes 13 to 29 in which the dendritic cells pulsed with the polypeptides having the amino acid sequences represented by SEQ ID NOs: 3 to 19 were used, as compared to the supernatants of Lanes 1 and 2 in which the dendritic cells not pulsed with any polypeptide and the dendritic cells pulsed with the negative control polypeptide, respectively, were used (FIG. 2). These results revealed that the peptides of SEQ ID NOs: 3 to 19 are T cell epitope peptides having an ability to specifically stimulate the proliferation of HLA-A0201-positive CD8-positive T cells, and to induce IFN-γ production. Further, it has also been revealed that the amounts of IFN-γ produced by T cells stimulated with these peptides were markedly higher than the amounts of IFN-γ produced by T cells stimulated with the known peptides which bind to the HLA-A0201 molecule and which have the amino acid sequences represented by SEQ ID NOs: 75 to 83 (Lanes 4 to 12), and with the full-length PDS5A protein consisting of the amino acid sequence represented by SEQ ID NO: 2 (Lane 3). In other words, these results indicate that the polypeptides of SEQ ID NOs: 3 to 19 have a markedly higher immune-inducing activity as compared to that of the peptides previously reported. In addition, although the sequences of SEQ ID NOs: 3 to 19 having the above described immune-inducing activity are included in the amino acid sequence of the full-length PDS5A protein represented by SEQ ID NO: 2, the amount of IFN-γ produced by the T cells stimulated with the full-length PDS5A protein of SEQ ID NO: 2 was low. The reason for this is thought to be that the full-length PDS5A protein failed to demonstrate sufficient immune-inducing activity, because the amino acid sequence of the full-length PDS5A protein also includes a number of sequences which inhibit the immunity-inducing activity.

Further, in order to examine the specificity of each of the peptide epitope-reactive CD8-positive T cells induced in Example 3 (2) using the polypeptides having the amino acid sequences represented by SEQ ID NOs: 20 to 34, to peptide epitopes, the amount of IFN-γ produced by the T cells, against dendritic cells expressing the HLA-A24 molecule, which dendritic cells had been pulsed with each of: the polypeptides of SEQ ID NOs: 20 to 34 (Lanes 4 to 18); the negative control polypeptide having the amino acid sequence represented by SEQ ID NO: 84; and the full-length PDS5A protein having the amino acid sequence represented by SEQ ID NO: 2; was measured by ELISA, in the same manner as described above.

Figure 3:
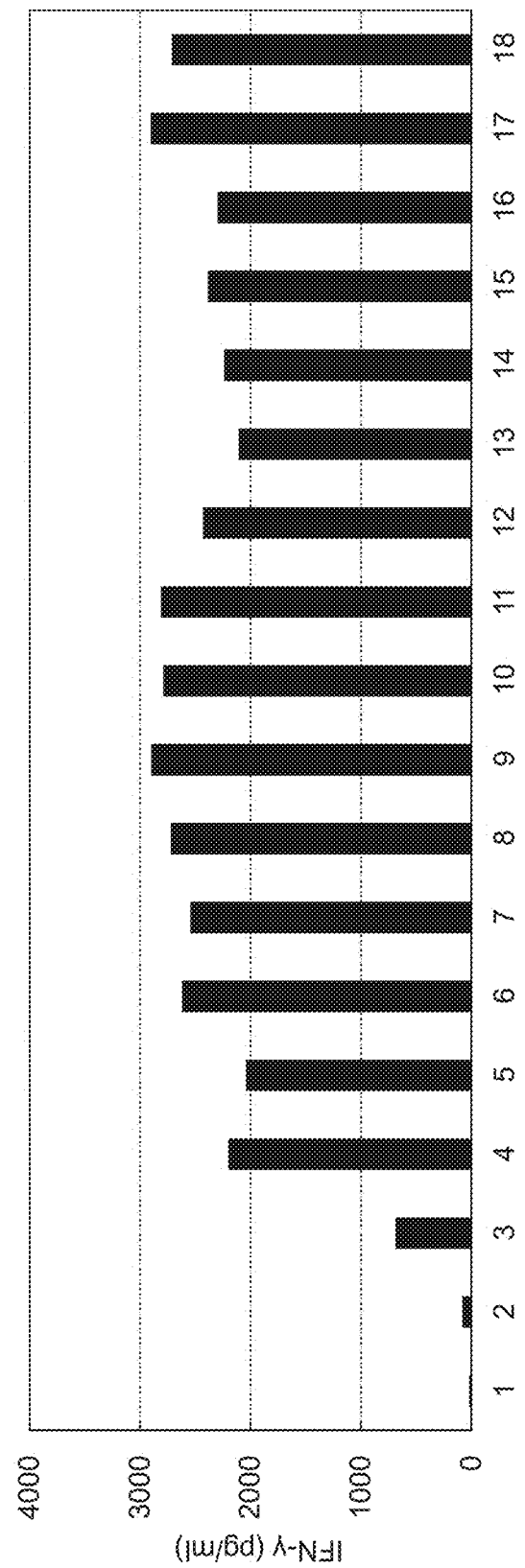
FIG. 3 shows that CD8-positive T cells specific to each of polypeptides consisting of the amino acid sequences represented by SEQ ID NOs: 20 to 34 recognize the complex consisting of the polypeptide and HLA-A24 and produce IFN-γ.

As a result, a markedly higher IFN-γ production was observed in the culture supernatants of Lanes 4 to 18 in which the dendritic cells pulsed with the polypeptides of SEQ ID NOs: 20 to 34 were used, as compared to the supernatants of Lanes 1 and 2 in which the dendritic cells not pulsed with any polypeptide and the dendritic cells pulsed with the negative control polypeptide, respectively, were used (Figure. 3).

These results revealed that the polypeptides of SEQ ID NOs: 20 to 34 are T cell epitope peptides having an ability to specifically stimulate the proliferation of HLA-A24-positive CD8-positive T cells, and to induce IFN-γ production. Further, it has also been revealed that that the amounts of IFN-γ produced by T cells stimulated with these polypeptides were markedly higher than the amounts of IFN-γ produced by T cells stimulated with the full-length PDS5A protein having the amino acid sequence represented by SEQ ID NO: 2. The reason for this is thought to be that the full-length PDS5A protein failed to demonstrate sufficient immunity-inducing activity, due to the same reason as described above.

(2) Cytotoxicity Assay

Subsequently, the following were examined: whether or not the polypeptides having the amino acid sequences represented by SEQ ID NOs: 3 to 19, which are used in the present invention, are presented on the HLA-A0201 molecules on tumor cells which are HLA-A0201-positive and which express human PDS5A protein; whether or not the CD8-positive T cells stimulated with the polypeptides according to the present invention can damage the tumor cells which are HLA-A0201-positive and which express the human PDS5A protein; and further, whether or not the above described CD8-positive T cells have a markedly higher ability to damage the tumor cells as compared to the CD8-positive T cells stimulated with the known peptides (SEQ ID NOs: 75 to 83) and those stimulated with the PDS5A protein.

Each of the total 10 types of cell lines whose expression of human PDS5A protein has been confirmed, namely: a human glioma (malignant brain tumor) cell line U251 cells; a leukemia cell line Jurkat cells; a liver cancer cell line SK-Hep1; a breast cancer cell line MCF7; a pancreatic cancer cell line Panc1; an ovarian cancer cell line OVCAR3; a renal cancer cell line A498; a colorectal cancer cell line HCT116; a stomach cancer cell line KATO3; and a lung cancer cell line NCI-H522 (purchased from ATCC); were collected into a 50 mL centrifugal tube, in an amount of 1×10⁶ cells each. After adding 100 μCi of chromium 51 thereto, the cells were incubated at 37° C. for 2 hours. Thereafter, each type of the cells were washed 3 times with RPMI medium (manufactured by Gibco Brl Co.) containing 10% fetal bovine serum (hereinafter, referred to as FBS; manufactured by Gibco Brl Co.) and placed in wells of a 96-well V-bottom plate at a population of 1×10³ cells per well. To each well, 5×10⁴ cells of HLA-A0201-positive CD8-positive T cells suspended in RPMI medium containing 10% FBS, which cells had been induced by stimulation with each of: the polypeptides having the amino acid sequences represented by SEQ ID NOs: 3 to 19, the negative control polypeptides (SEQ ID NO: 74), the known peptides (SEQ ID NOs: 75 to 83) and the full-length PDS5A protein having the amino acid sequence represented by SEQ ID NO: 2; were further added, followed by culturing for 4 hours under the conditions of 37° C. and 5% CO₂. After the cultivation, the amount of chromium 51 released from the damaged tumor cells into each culture supernatant was measured, whereby the cytotoxic activity of the CD8-positive T cells induced by stimulation with each of the polypeptides and the protein was calculated.

Figure 4A:
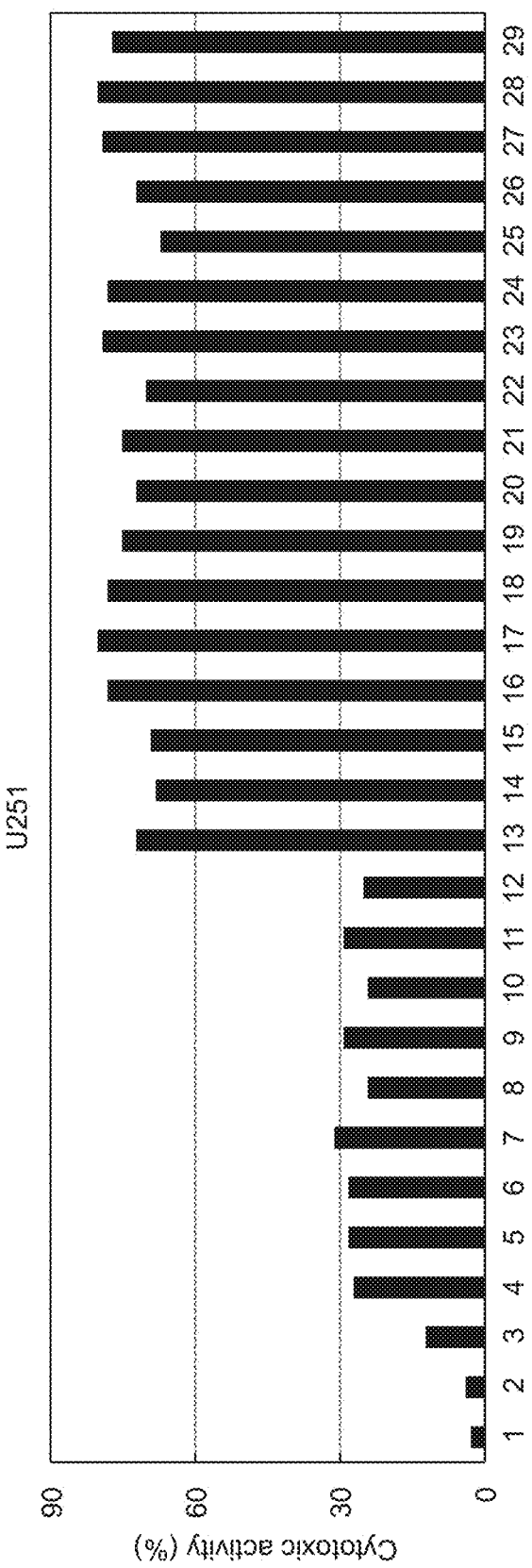
FIG. 4A shows the cytotoxic activity, against cancer cells, of CD8-positive T cells specific to each of the polypeptides consisting of the amino acid sequences represented by SEQ ID NOs: 3 to 19.
Figure 4B:
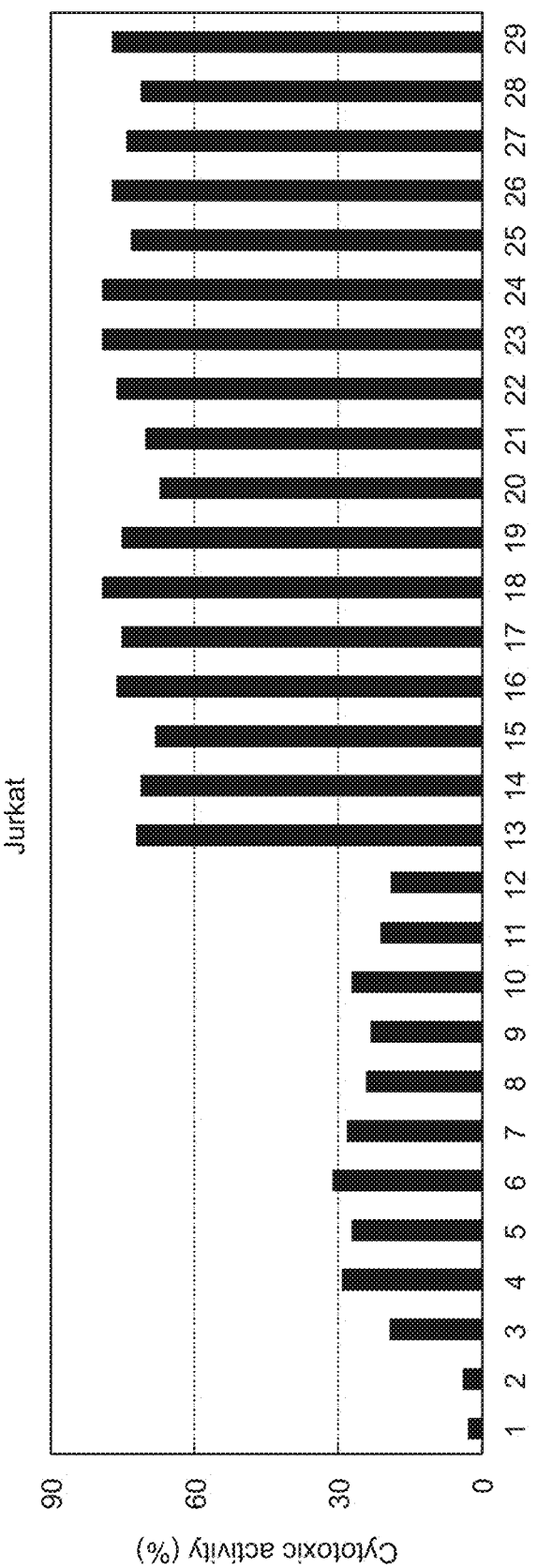
FIG. 4B shows the cytotoxic activity, against cancer cells, of CD8-positive T cells specific to each of the polypeptides consisting of the amino acid sequences represented by SEQ ID NOs: 3 to 19.

As a result, it has been revealed that the HLA-A0201-positive CD8-positive T cells induced by stimulation with the polypeptides having the amino acid sequences represented by SEQ ID NOs: 3 to 19 exhibit a markedly high cytotoxic activity, which is well above the generally predictable range, against all of the above described 10 types of cells. As representative examples, the cytotoxic activity against the U251 cells and the Jurkat cells are shown in FIG. 4A and FIG. 4B, respectively. It can be seen that the CD8-positive T cells stimulated by the polypeptides having the amino acid sequences represented by SEQ ID NOs: 3 to 19 (Lanes 13 to 29, respectively) exhibit a markedly higher cytotoxic activity against the U251 cells and the Jurkat cells, as compared to the CD8-positive T cells stimulated by the polypeptides having the amino acid sequences represented by SEQ ID NOs: 75 to 83 (Lanes 4 to 12, respectively), and those stimulated by the full-length PDS5A protein (Lane 3). On the other hand, the CD8-positive T cells induced with the negative control polypeptide (Lane 2) did not show any cytotoxic activity, the result being roughly the same as the case of Mock (Lane 1). These results suggest that each of the polypeptides of SEQ ID NOs: 3 to 19 used in the present invention is presented on the HLA-A0201 molecules on tumor cells which are HLA-A0201-positive and which express human PDS5A polypeptide, and in addition, that the polypeptides according to the present invention have an ability to induce CD8-positive cytotoxic T cells capable of damaging such tumor cells, to a level well above a predictable range. Further, regardless of the fact that the amino acid sequence of the full-length PDS5A protein includes the sequences of SEQ ID NOs: 3 to 19, the CD8-positive T cells stimulated with the full-length PDS5A protein exhibited a markedly lower cytotoxic activity, as compared to that of the CD8-positive T cells stimulated with the polypeptides having the amino acid sequences of SEQ ID NOs: 3 to 19 (Lanes 3, 13 to 29). The reason for this is thought to be that the PDS5A protein failed to induce T cells having a high cytotoxic activity, because the amino acid sequence of the PDS5A protein includes a number of sequences which inhibit the immunity-inducing activity.

Similarly, it was examined whether or not the polypeptides of SEQ ID NOs: 20 to 34 are presented on the HLA-A24 molecules on tumor cells which are HLA-A24-positive and which express human PDS5A protein; whether or not the CD8-positive T cells stimulated with the polypeptides according to the present invention can damage the tumor cells which are HLA-A24-positive and which express the human PDS5A protein; and further, whether or not the above described CD8-positive T cells have a markedly higher ability to damage the tumor cells as compared to the CD8-positive T cells stimulated with the PDS5A protein.

Chromium 51 was allowed to be incorporated into the total 6 types of cell lines which are HLA-A24-positive and which express human PDS5A protein, namely: a leukemia cell line THP1; a human glioma cell line KNS-42; a liver cancer cell line SK-Hep1; a renal cancer cell line Caki1; a colorectal cancer cell line SW480; and a stomach cancer cell line KATO3 (purchased from RIKEN and ATCC). Each type of the cells were cultured with the HLA-A24-positive CD8-positive T cells which had been induced by stimulation with each of: the polypeptides having the amino acid sequences represented by SEQ ID NOs: 20 to 34; the negative control polypeptide (SEQ ID NO: 84); and the full-length PDS5A protein, and the amount of chromium 51 released from the damaged cells into each culture supernatant was measured.

Figure 5A:
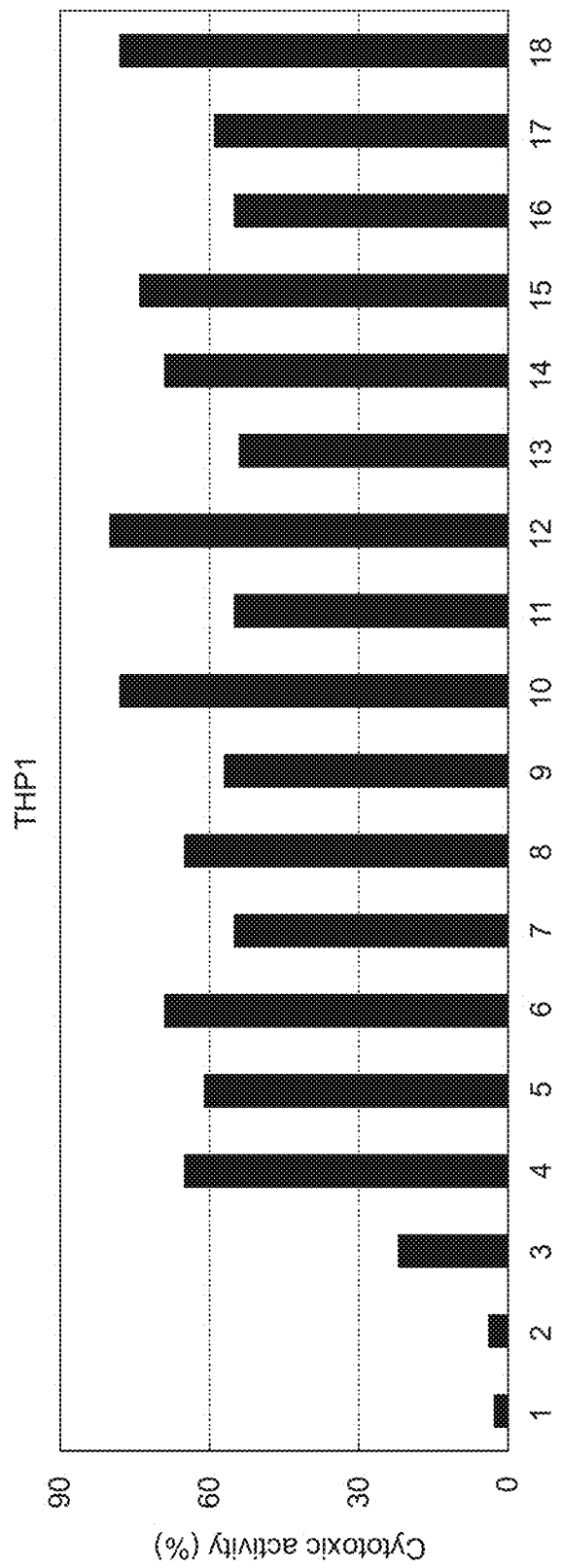
FIG. 5A is a graph showing the cytotoxic activity, against cancer cells, of CD8-positive T cells specific to each of the polypeptides consisting of the amino acid sequences represented by SEQ ID NOs: 20 to 34.
Figure 5B:
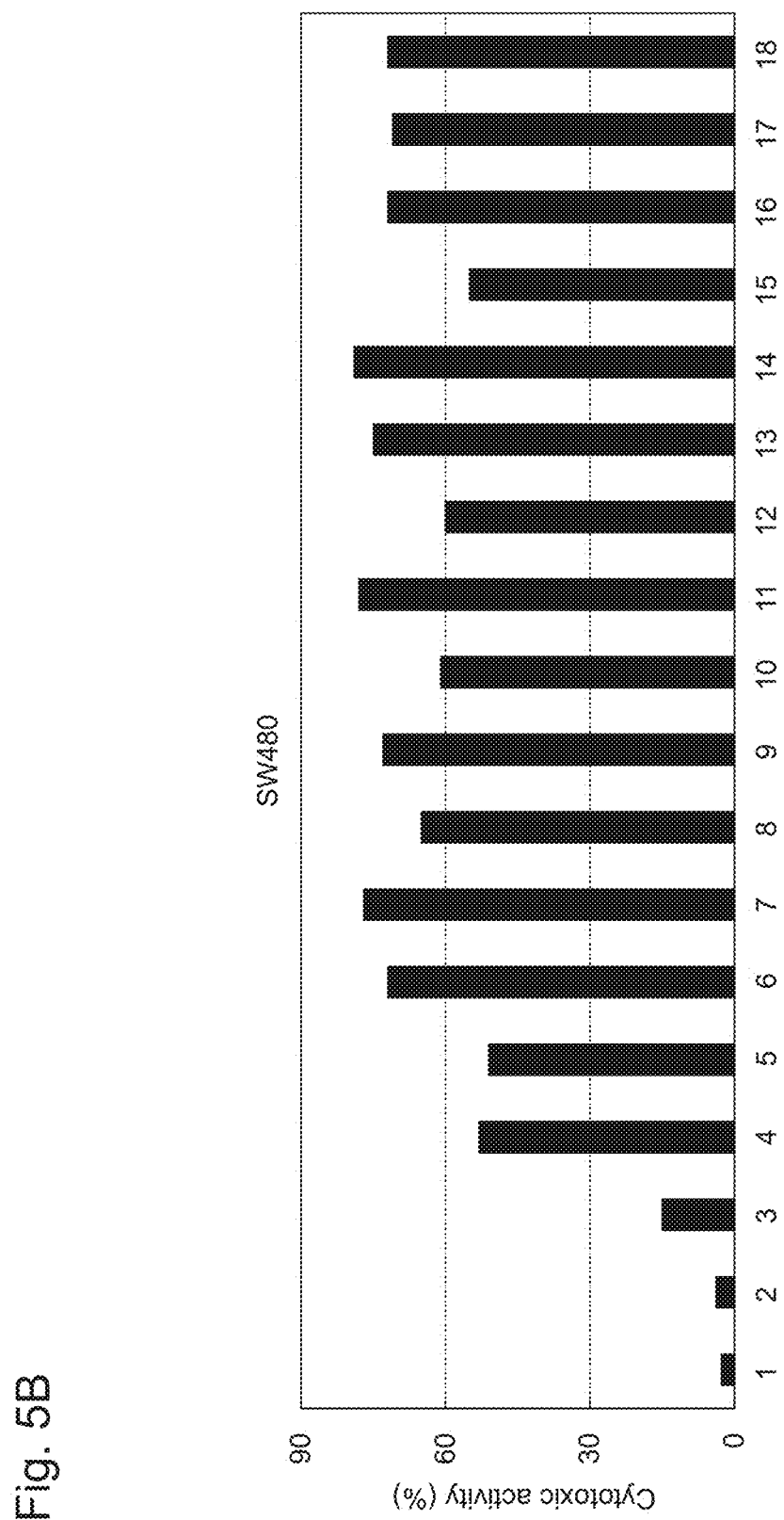
FIG. 5B shows the cytotoxic activity, against cancer cells, of CD8-positive T cells specific to each of the peptides consisting of the amino acid sequences represented by SEQ ID NOs: 20 to 34.

As a result, it has been revealed that the HLA-A24-positive CD8-positive T cells stimulated with the polypeptides having the amino acid sequences represented by SEQ ID NOs: 20 to 34 exhibit a markedly high cytotoxic activity, which is well above the generally predictable range, against all types of cancer cells used. As representative examples, the cytotoxic activity against the THP1 cells and the SW480 cells are shown in FIG. 5A and FIG. 5B, respectively. It can be seen that the CD8-positive T cells stimulated by the polypeptides having the amino acid sequences represented by SEQ ID NOs: 20 to 34 (Lanes 4 to 18, respectively) exhibit a markedly higher cytotoxic activity against the THP1 cells and the SW480 cells, as compared to the CD8-positive T cells (Lane 3) stimulated by the full-length PDS5A protein. On the other hand, the CD8-positive T cells induced with the negative control polypeptide (Lane 2) did not show any cytotoxic activity, the result being roughly the same as the case of Mock (Lane 1). Thus, it can be seen that each of the polypeptides of SEQ ID NOs: 20 to 34 is presented on the HLA-A24 molecules on cells which are HLA-A24-positive and which express human PDS5A protein, and these results suggest that the polypeptides according to the present invention have an ability to induce CD8-positive cytotoxic T cells capable of damaging such cells.

On the other hand, when the above described 14 types of cancer cells were exposed to the polypeptides represented by the amino acid sequences of SEQ ID NOs: 3 to 34 and the full-length PDS5A protein consisting of the amino acid sequence represented by SEQ ID NO: 2, no cancer cells were killed at all. This confirmed the fact that these polypeptides do not have an activity to directly kill the cancer cells.

The cytotoxic activity was determined as described above, by mixing $5 \times 10^4$ cells of the CD8-positive T cells stimulated and induced with each of the polypeptides used in the present invention and $1 \times 10^3$ cells of each type of the tumor cells into which chromium 51 was incorporated; culturing each mixture of cells for 4 hours; measuring the amount of chromium 51 released into each culture medium after the cultivation; and calculating the cytotoxic activity of the CD8-positive T cells against each type of the tumor cells (referred to as target cells) according to the following formula*.

*Formula: cytotoxic activity (%)=amount of chromium 51 released from target cells upon addition of CD8-positive T cells/amount of chromium 51 released from target cells upon addition of 1 N hydrochloric acid×100

Example 4: Induction of CD4-Positive T Cells Reactive with Peptide Epitopes Derived from PDS5A Protein—Derived Peptide For predicting CD4-positive T cell antigen epitopes, the amino acid sequence of the human PDS5A protein was analyzed with a computer-based prediction program using the SYFPEITHI algorithm (by Rammensee), and 33 types of peptides represented by SEQ ID NOs: 35 to 67 and expected to be HLA class II-binding peptides were selected. All the selected peptides were synthesized by Greiner Japan Co. Ltd. that provides custom peptide synthesis services.

Peripheral blood was separated from the blood of an HLA-DRB1*04-positive healthy individual. The peripheral blood was layered on Lymphocyte separation medium (manufactured by Organon Teknika Corporation), and centrifuged at 1,500 rpm at room temperature for 20 minutes. A PBMC-containing fraction was collected and washed 3 times (or more) with a cold phosphate buffer solution to obtain PBMCs. The thus obtained PBMCs were suspended in 20 mL of AIM-V medium (manufactured by Life Technologies, Inc.), and allowed to adhere to a culture flask (manufactured by Falcon Plastics Co.) for 2 hours under the conditions of 37° C. and 5% $CO_2$. Non-adherent cells were used for the preparation of T cells, and adherent cells were used for preparing dendritic cells.

The adherent cells were cultured in AIM-V medium in the presence of IL-4 (1,000 U/ml) and GM-CSF (1,000 U/ml). Six days later, the medium was replaced with AIM-V medium supplemented with IL-4 (1,000 U/mL), GM-CSF (1,000 U/mL), IL-6 (1,000 U/mL, manufactured by Genzyme Corporation), IL-1β (10 ng/mL, manufactured by Genzyme Corporation) and TNF-α (10 ng/mL, manufactured by Genzyme Corporation), and the cells were cultured for another 2 days. The obtained population of the non-adherent cells was used as the dendritic cells.

The thus prepared dendritic cells were suspended in AIM-V medium at a cell density of $1 \times 10^6$ cells/mL. Each of the polypeptides of SEQ ID NOs: 35 to 67, the negative control polypeptide (SEQ ID NO: 85) and the PDS5A protein consisting of the amino acid sequence represented by SEQ ID NO: 2 was added to the cells at a concentration of 10 mg/mL, followed by culturing for 4 hours under the conditions of 37° C. and 5% $CO_2$, using a 96-well plate. After the cultivation, the cells were irradiated with X-ray (3000 rad), washed with AIM-V medium, suspended in AIM-V medium containing 10% human AB serum (manufactured by Nabi Biopharmaceuticals Inc.), IL-6 (1,000

U/mL) and IL-12 (10 ng/mL, manufactured by Genzyme Corporation), and then placed in wells of a 24-well plate at a population of 1×10⁵ cells per well. Further, the prepared T cell population was added to the wells at a population of 1×10⁶ cells per well, and the cells were cultured under the conditions of 37° C. and 5% $CO_2$. Seven days later, each culture supernatant was discarded. Then, dendritic cells treated with each peptide obtained in the same manner as described above or the PDS5A protein followed by X-ray irradiation were suspended in AIM-V medium containing 10% human AB serum (manufactured by Nabi Biopharmaceuticals Inc.) and IL-2 (10 U/mL, manufactured by Genzyme Corporation), and the resulting suspension was added to the wells of the 24-well plate at a population of 1×10⁵ cells per well, followed by further culturing the cells. The same procedures were repeated 4 times at intervals of 7 days, and the stimulated T cells were then collected. Thereafter, the induction of CD4-positive T cells was confirmed by flow cytometry. As a result, the induced T cells in each well were confirmed to be proliferated.

Example 5: Determination of PDS5A Protein-Derived Helper T Cell Antigen Epitopes which Stimulate HLA-DRB1*04-Positive CD4-Positive T Cells In order to examine the specificity of the respective CD4-positive T cells induced in the above described Example 4 to the respective peptide proteins, the PBMCs expressing HLA-DRB1*04 molecules were pulsed with various types of polypeptides. The PBMCs were prepared by culturing in AIM-V medium supplemented with each polypeptide at a concentration of 10 μg/mL under the conditions of 37° C. and 5% $CO_2$ for 4 hours. As the various types of polypeptides, the respective polypeptides represented by the amino acid sequences of SEQ ID NOs: 35 to 67, the negative control polypeptide (SEQ ID NO: 85) and the full-length PDS5A protein consisting of the amino acid sequence represented by SEQ ID NO: 2 were used. To 5×10⁴ PBMCs which had been pulsed with each peptide, 5×10⁴ CD4-positive T cells were added, and the cells were cultured for 24 hours in AIM-V medium containing 10% human AB serum, in a 96-well plate. Each supernatant after the cultivation was collected, and the amount of produced IFN-γ was measured by ELISA.

As a result, an IFN-γ production of 1,000 pg/mL or more was confirmed in the culture supernatants in the wells of PBMCs pulsed with the respective peptides of SEQ ID NOs: 35 to 67. On the other hand, the production of IFN-γ was barely observed in the culture supernatants in the well of PBMCs pulsed with the negative control polypeptide and in the well of the dendritic cells alone not pulsed with any polypeptide. Thus, it has been revealed that the polypeptides represented by the amino acid sequences SEQ ID NOs: 35 to 67 are T cell epitope peptides having an ability to specifically stimulate and propagate the HLA-DRB1*04-positive CD4-positive T cells, and to induce the production of IFN-γ. Further, regardless of the fact that the amino acid sequence of the full-length PDS5A protein includes the above described sequences of SEQ ID NOs: 35 to 67 having an immunity-inducing activity, the amount of IFN-γ produced in the culture supernatant in the well of PBMC cells pulsed with the full-length PDS5A protein was extremely low. The reason for this is thought to be that the PDS5A protein failed to demonstrate sufficient immunity-inducing activity, because the amino acid sequence of the PDS5A protein includes a number of sequences which inhibit the immunity-inducing activity.

Subsequently, it was examined whether or not the polypeptides of SEQ ID NOs: 35 to 67 having an ability to stimulate the proliferation of the HLA-DRB1*04-positive T cells are epitopes which are naturally processed from the PDS5A protein within the antigen-presenting cells and presented on HLA-DR. A lysate of HEK293 cells (purchased from ATCC) transiently expressing the PDS5A protein was added to immature dendritic cells to allow the digestion of the protein, and the maturation of the dendritic cells. Then, it was examined whether or not the T cells stimulated with each of the polypeptides of SEQ ID NOs: 35 to 67, the negative control polypeptide and the PDS5A protein are stimulated by the resulting dendritic cells. Peripheral blood was separated from the blood of an HLA-DRB1*04-positive healthy individual. The peripheral blood was layered on Lymphocyte separation medium, and centrifuged at 1,500 rpm at room temperature for 20 minutes. The interphase containing PBMCs was collected and washed 3 times (or more) with a cold phosphate buffer solution to obtain PBMCs. The thus obtained PBMCs were suspended in 20 mL of AIM-V medium, and allowed to adhere to a culture flask (manufactured by Falcon Plastics Co.) for 2 hours under the conditions of 37° C. and 5% $CO_2$. The adherent cells were cultured in AIM-V medium in the presence of IL-4 (1,000 U/mL) and GM-CSF (1,000 U/mL) for 6 days, to obtain immature dendritic cells. The above described lysate was added to 5×10⁵ immature dendritic cells, followed by culturing in AIM-V medium supplemented with IL-4 (1,000 U/mL), GM-CSF (1,000 U/mL), IL-6 (1,000 U/mL), IL-1β (10 ng/mL) and TNF-α (10 ng/mL) for 2 days. The cultured dendritic cells were irradiated with X-ray (3000 rad), washed with AIM-V medium, suspended in AIM-V medium containing 10% human AB serum, and then placed in wells of a 96-well plate at a population of 3.3×10⁴ cells per well. To each well, 5×10⁴ T cells stimulated with each of the polypeptides of SEQ ID NOs: 35 to 67, the negative control polypeptide and the PDS5A protein were added, and the cells were cultured under the conditions of 37° C. and 5% $CO_2$ for 24 hours. Each supernatant after the cultivation was collected, and the amount of produced IFN-γ was measured by ELISA.

Figure 6:
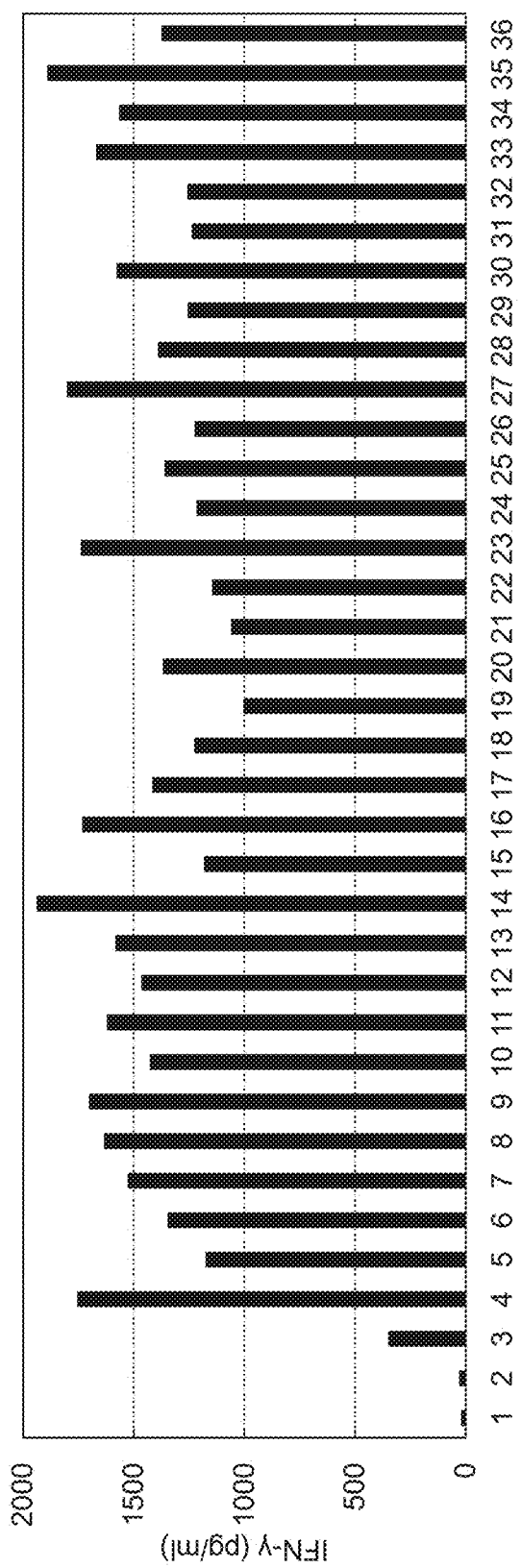
FIG. 6 is a graph showing that CD4-positive T cells specific to each of the polypeptides consisting of the amino acid sequences represented by SEQ ID NOs: 35 to 67 recognize the complex of the polypeptide and HLA-DRB1*04 and produce IFN-γ.

As a result, as shown in FIG. 6, it has been found out that the T cells of Lanes 4 to 36 which were stimulated with the polypeptides of SEQ ID NOs: 35 to 67, respectively, produced IFN-γ in response to stimulation by the dendritic cells to which the PDS5A protein was added. On the other hand, the production of IFN-γ was barely observed in the T cells of Lane 2 stimulated with the negative control polypeptide and the T cells of Lane 1 not stimulated with any polypeptide. Thus, it has been revealed that the polypeptides of SEQ ID NOs: 35 to 67 are epitopes which are naturally processed from the PDS5A protein within the antigen-presenting cells and presented on HLA-DR. Further, the production of IFN-γ in the T cells of Lane 3 pulsed with the full-length PDS5A protein was extremely low, also in the present experiment. The reason for this is thought to be that the full-length PDS5A protein failed to demonstrate sufficient immunity-inducing activity, because the amino acid sequence of the full-length PDS5A protein includes a number of sequences which inhibit the immunity-inducing activity.

INDUSTRIAL APPLICABILITY

The immune inducer according to the present invention containing a polypeptide which exhibits an anti-tumor activity against various types of cancers is useful in the treatment or prevention of cancer, or in the detection of cancer.

All publications, patents, and patent applications cited in this specification are incorporated herein by reference in their entirety.

The invention claimed is:

1. A composition comprising a polypeptide having an immune-inducing activity and selected from the group of polypeptides consisting of the amino acid sequences represented by SEQ ID NOs: 3 and 4.

* * * * *

SEQUENCE LISTING

<160> NUMBER OF SEQ ID NOS: 86

<210> SEQ ID NO 1
<211> LENGTH: 7190
<212> TYPE: DNA
<213> ORGANISM: Homo sapiens
<220> FEATURE:
<221> NAME/KEY: CDS
<222> LOCATION: (541)..(4554)

<400> SEQUENCE: 1

```
ggccggcgga ggaagggag ggagcgagga gcgcgcgctg ctctcgcgtg ctctcgcgcc      60
gctcgcgtga ccggccggtg tgtgcgcgag gccccggctc ccggggcacg gacggccggg     120
cgcgcgcctc tgcgagggc gtccgggtcc gagtcggcgg tccggccgg cgcgaggtgc      180 gtgcgggcgg gccgcggggg tcccggacgg acacaagcgc acacactccc ggaggagcct    240
tcgaggctgc tcttcctcgg ccagacggag agcggcactg tctccccgcc cagcgctcac    300
tcgccccgcg tctcccccg cggcggctgc tcctcctcgg caccgccagc cccagcgccg    360
ctcccgggcg ggcgggcggc ggcggcggcg cggcgggac ccgcggagcc gctttgtgtg     420
cagcccgact aggggcggcg gcgcaaccac ctgacagagg cccgggcgct cgatgcacct    480
tccgcccgca tgaggaggag aggccggtag aggactgtga accaaaagtt gtccccagg    540
```

```
atg gac ttc acc gcg cag ccc aag cct gcc act gcc ctc tgt ggc gtc       588
Met Asp Phe Thr Ala Gln Pro Lys Pro Ala Thr Ala Leu Cys Gly Val
1               5                  10                  15 gtg agt gcc gac ggg aag atc gct tac cct ccg ggg gta aaa gag atc       636
Val Ser Ala Asp Gly Lys Ile Ala Tyr Pro Pro Gly Val Lys Glu Ile
            20                  25                  30 acc gac aag atc acc acg gac gag atg atc aaa cgc ctg aag atg gta       684
Thr Asp Lys Ile Thr Thr Asp Glu Met Ile Lys Arg Leu Lys Met Val
        35                  40                  45 gtg aaa acc ttt atg gat atg gat cag gac tca gaa gat gaa aaa cag       732
Val Lys Thr Phe Met Asp Met Asp Gln Asp Ser Glu Asp Glu Lys Gln
    50                  55                  60 cag tat ctc cca cta gcc ttg cat ctt gca tct gaa ttc ttc ctc agg       780
Gln Tyr Leu Pro Leu Ala Leu His Leu Ala Ser Glu Phe Phe Leu Arg
65                  70                  75                  80 aac ccc aat aaa gat gtg cgt ctc ctt gta gca tgt tgt ttg gct gat       828
Asn Pro Asn Lys Asp Val Arg Leu Leu Val Ala Cys Cys Leu Ala Asp
                85                  90                  95 atc ttt cgt atc tat gcc cca gaa gct cca tat act tcc cat gat aaa       876
Ile Phe Arg Ile Tyr Ala Pro Glu Ala Pro Tyr Thr Ser His Asp Lys
            100                 105                 110 ctt aag gac ata ttt ttg ttt att acc aga caa tta aaa ggt ttg gag       924
Leu Lys Asp Ile Phe Leu Phe Ile Thr Arg Gln Leu Lys Gly Leu Glu
        115                 120                 125 gat aca aag agt cca cag ttt aat aga tac ttt tat tta tta gag aat       972
Asp Thr Lys Ser Pro Gln Phe Asn Arg Tyr Phe Tyr Leu Leu Glu Asn
    130                 135                 140 tta gct tgg gtt aaa tca tat aac atc tgc ttt gaa ttg gaa gat tgc      1020
Leu Ala Trp Val Lys Ser Tyr Asn Ile Cys Phe Glu Leu Glu Asp Cys
145                 150                 155                 160 aat gaa att ttt att cag ctt ttt aga act ctc ttc tca gtg atc aac      1068
Asn Glu Ile Phe Ile Gln Leu Phe Arg Thr Leu Phe Ser Val Ile Asn
                165                 170                 175 aat agc cac aat aag aag gta caa atg cac atg cta gat ttg atg agt      1116
Asn Ser His Asn Lys Lys Val Gln Met His Met Leu Asp Leu Met Ser
            180                 185                 190
```

```
tct atc atc atg gaa ggt gat gga gtt act caa gaa tta ttg gac tcc     1164
Ser Ile Ile Met Glu Gly Asp Gly Val Thr Gln Glu Leu Leu Asp Ser
        195                 200                 205 att ctt att aac ctc att cct gca cat aag aac tta aat aaa cag tcc     1212
Ile Leu Ile Asn Leu Ile Pro Ala His Lys Asn Leu Asn Lys Gln Ser
210                 215                 220 ttt gac ctt gca aaa gtg cta ttg aaa aga aca gtc cag act att gag     1260
Phe Asp Leu Ala Lys Val Leu Leu Lys Arg Thr Val Gln Thr Ile Glu
225                 230                 235                 240 gca tgc att gct aat ttt ttc aat caa gtc ctg gtg ctg gga aga tca     1308
Ala Cys Ile Ala Asn Phe Phe Asn Gln Val Leu Val Leu Gly Arg Ser
            245                 250                 255 tca gta agt gat ttg tca gaa cat gta ttt gat ctg att cag gaa ctt     1356
Ser Val Ser Asp Leu Ser Glu His Val Phe Asp Leu Ile Gln Glu Leu
        260                 265                 270 ttt gct ata gat cct cat tta tta tta tcc gtc atg cca cag ctt gaa     1404
Phe Ala Ile Asp Pro His Leu Leu Leu Ser Val Met Pro Gln Leu Glu
    275                 280                 285 ttc aaa cta aag agc aat gat gga gaa gag cga tta gct gtt gtt cga     1452
Phe Lys Leu Lys Ser Asn Asp Gly Glu Glu Arg Leu Ala Val Val Arg
290                 295                 300 ctt cta gct aaa ttg ttt ggc tcc aaa gat tct gat ttg gca aca cag     1500
Leu Leu Ala Lys Leu Phe Gly Ser Lys Asp Ser Asp Leu Ala Thr Gln
305                 310                 315                 320 aat cgt cct ctt tgg caa tgt ttt ctt gga cga ttt aat gat att cat     1548
Asn Arg Pro Leu Trp Gln Cys Phe Leu Gly Arg Phe Asn Asp Ile His
            325                 330                 335 gtt cct gtg aga tta gaa agt gtg aaa ttt gcc agt cat tgt tta atg     1596
Val Pro Val Arg Leu Glu Ser Val Lys Phe Ala Ser His Cys Leu Met
        340                 345                 350 aat cac cca gat tta gcg aag gat ctc aca gaa tat tta aag gtt aga     1644
Asn His Pro Asp Leu Ala Lys Asp Leu Thr Glu Tyr Leu Lys Val Arg
    355                 360                 365 tca cat gat cca gaa gaa gct att cgt cat gat gtc att gtt act ata     1692
Ser His Asp Pro Glu Glu Ala Ile Arg His Asp Val Ile Val Thr Ile
370                 375                 380 ata aca gct gcc aag agg gac ctg gcc tta gta aat gat cag ctg ctt     1740
Ile Thr Ala Ala Lys Arg Asp Leu Ala Leu Val Asn Asp Gln Leu Leu
385                 390                 395                 400 ggc ttt gta agg gaa aga aca ctg gat aaa cgg tgg cga gta aga aaa     1788
Gly Phe Val Arg Glu Arg Thr Leu Asp Lys Arg Trp Arg Val Arg Lys
            405                 410                 415 gaa gct atg atg ggt ctg gct cag ctt tat aag aaa tac tgt ctt cat     1836
Glu Ala Met Met Gly Leu Ala Gln Leu Tyr Lys Lys Tyr Cys Leu His
        420                 425                 430 ggt gaa gca gga aag gaa gct gca gag aaa gtc agc tgg ata aag gac     1884
Gly Glu Ala Gly Lys Glu Ala Ala Glu Lys Val Ser Trp Ile Lys Asp
    435                 440                 445 aaa ctt ctg cat att tat tat cag aac agc att gac gac aaa ctg ttg     1932
Lys Leu Leu His Ile Tyr Tyr Gln Asn Ser Ile Asp Asp Lys Leu Leu
450                 455                 460 gta gag aaa atc ttt gct cag tat ctt gtc ccc cac aac ctg gaa aca     1980
Val Glu Lys Ile Phe Ala Gln Tyr Leu Val Pro His Asn Leu Glu Thr
465                 470                 475                 480 gaa gag aga atg aaa tgc tta tat tac tta tat gct agt ttg gat cca     2028
Glu Glu Arg Met Lys Cys Leu Tyr Tyr Leu Tyr Ala Ser Leu Asp Pro
            485                 490                 495 aat gct gta aaa gct ctc aac gaa atg tgg aag tgt cag aac atg ctt     2076
Asn Ala Val Lys Ala Leu Asn Glu Met Trp Lys Cys Gln Asn Met Leu
        500                 505                 510
```

```
cgg agc cat gta cgc gaa cta ttg gat ttg cac aag cag cct aca tca    2124
Arg Ser His Val Arg Glu Leu Leu Asp Leu His Lys Gln Pro Thr Ser
        515                 520                 525 gag gct aac tgt tct gcc atg ttt gga aaa ctg atg acc ata gca aag    2172
Glu Ala Asn Cys Ser Ala Met Phe Gly Lys Leu Met Thr Ile Ala Lys
    530                 535                 540 aat ttg cct gac ccc ggg aaa gca caa gat ttt gtg aag aaa ttt aac    2220
Asn Leu Pro Asp Pro Gly Lys Ala Gln Asp Phe Val Lys Lys Phe Asn
545                 550                 555                 560 cag gtt ctc ggc gat gat gag aaa ctt cgg tct cag ttg gag tta tta    2268
Gln Val Leu Gly Asp Asp Glu Lys Leu Arg Ser Gln Leu Glu Leu Leu
                565                 570                 575 att agc cca acc tgt tct tgc aaa caa gca gat att tgt gtg aga gaa    2316
Ile Ser Pro Thr Cys Ser Cys Lys Gln Ala Asp Ile Cys Val Arg Glu
            580                 585                 590 ata gcc cgg aaa ctt gca aat cct aag caa cca aca aat cct ttt cta    2364
Ile Ala Arg Lys Leu Ala Asn Pro Lys Gln Pro Thr Asn Pro Phe Leu
        595                 600                 605 gag atg gtc aaa ttt ctg ttg gaa aga atc gca cct gtg cac att gat    2412
Glu Met Val Lys Phe Leu Leu Glu Arg Ile Ala Pro Val His Ile Asp
    610                 615                 620 tca gaa gcc ata agt gca cta gtg aaa ttg atg aat aag tca ata gag    2460
Ser Glu Ala Ile Ser Ala Leu Val Lys Leu Met Asn Lys Ser Ile Glu
625                 630                 635                 640 ggg aca gca gat gat gaa gag gag ggt gta agt cca gat aca gct atc    2508
Gly Thr Ala Asp Asp Glu Glu Glu Gly Val Ser Pro Asp Thr Ala Ile
                645                 650                 655 cgt tca gga ctt gaa ctt ctt aag gtt ctg tct ttt aca cat cct acc    2556
Arg Ser Gly Leu Glu Leu Leu Lys Val Leu Ser Phe Thr His Pro Thr
            660                 665                 670 tcg ttc cac tct gca gag aca tat gag tcc ttg tta cag tgc cta aga    2604
Ser Phe His Ser Ala Glu Thr Tyr Glu Ser Leu Leu Gln Cys Leu Arg
        675                 680                 685 atg gag gat gac aag gta gca gaa gct gct att caa att ttt aga aat    2652
Met Glu Asp Asp Lys Val Ala Glu Ala Ala Ile Gln Ile Phe Arg Asn
    690                 695                 700 aca ggt cac aaa ata gaa aca gac ctt ccc cag ata cga tcg acc tta    2700
Thr Gly His Lys Ile Glu Thr Asp Leu Pro Gln Ile Arg Ser Thr Leu
705                 710                 715                 720 att ccc att tta cat caa aaa gca aag agg ggt act cca cac caa gca    2748
Ile Pro Ile Leu His Gln Lys Ala Lys Arg Gly Thr Pro His Gln Ala
                725                 730                 735 aaa cag gct gtg cac tgt ata cac gcc ata ttc aca aat aaa gaa gtc    2796
Lys Gln Ala Val His Cys Ile His Ala Ile Phe Thr Asn Lys Glu Val
            740                 745                 750 cag ctt gca cag att ttt gag cca ctc agt agg agt ctg aat gct gat    2844
Gln Leu Ala Gln Ile Phe Glu Pro Leu Ser Arg Ser Leu Asn Ala Asp
        755                 760                 765 gtg cca gaa caa ctt ata act cca tta gtt tca ttg ggc cac att tct    2892
Val Pro Glu Gln Leu Ile Thr Pro Leu Val Ser Leu Gly His Ile Ser
    770                 775                 780 atg tta gca cca gat cag ttt gct tcc cca atg aaa tct gta gta gca    2940
Met Leu Ala Pro Asp Gln Phe Ala Ser Pro Met Lys Ser Val Val Ala
785                 790                 795                 800 aat ttt att gtg aaa gat ctg cta atg aat gac agg tca aca ggt gaa    2988
Asn Phe Ile Val Lys Asp Leu Leu Met Asn Asp Arg Ser Thr Gly Glu
                805                 810                 815 aag aat gga aaa ctg tgg tct cca gat gaa gag gtt tcc cct gaa gta    3036
Lys Asn Gly Lys Leu Trp Ser Pro Asp Glu Glu Val Ser Pro Glu Val
```

-continued

```
              820                 825                 830
cta gca aag gta cag gca att aaa ctt ctg gta agg tgg ctg ttg ggt   3084
Leu Ala Lys Val Gln Ala Ile Lys Leu Leu Val Arg Trp Leu Leu Gly
        835                 840                 845 atg aaa aac aac cag tct aaa tct gcc aat tca acc ctt cgg tta tta   3132
Met Lys Asn Asn Gln Ser Lys Ser Ala Asn Ser Thr Leu Arg Leu Leu
850                 855                 860 tca gcg atg ttg gtt agt gag ggt gac ctg aca gag caa aag agg atc   3180
Ser Ala Met Leu Val Ser Glu Gly Asp Leu Thr Glu Gln Lys Arg Ile
865                 870                 875                 880 agt aaa tct gat atg tct cgc ttg cga tta gct gct ggt agt gcc ata   3228
Ser Lys Ser Asp Met Ser Arg Leu Arg Leu Ala Ala Gly Ser Ala Ile
                885                 890                 895 atg aag ctt gct cag gaa cct tgt tac cat gaa att att acc cca gaa   3276
Met Lys Leu Ala Gln Glu Pro Cys Tyr His Glu Ile Ile Thr Pro Glu
        900                 905                 910 cag ttt cag ctc tgt gca ctt gtt att aat gat gag tgt tac caa gta   3324
Gln Phe Gln Leu Cys Ala Leu Val Ile Asn Asp Glu Cys Tyr Gln Val
        915                 920                 925 agg cag ata ttt gct cag aag ctg cat aag gca ctt gtg aag tta ctg   3372
Arg Gln Ile Phe Ala Gln Lys Leu His Lys Ala Leu Val Lys Leu Leu
930                 935                 940 ctc cca ttg gag tat atg gcg atc ttt gcc ttg tgt gcc aaa gat cct   3420
Leu Pro Leu Glu Tyr Met Ala Ile Phe Ala Leu Cys Ala Lys Asp Pro
945                 950                 955                 960 gtg aag gag aga aga gca cac gca cga caa tgt tta ctg aaa aat atc   3468
Val Lys Glu Arg Arg Ala His Ala Arg Gln Cys Leu Leu Lys Asn Ile
                965                 970                 975 agt ata cgc agg gaa tac att aag cag aat cct atg gct act gag aaa   3516
Ser Ile Arg Arg Glu Tyr Ile Lys Gln Asn Pro Met Ala Thr Glu Lys
        980                 985                 990 tta tta tca ctg ttg cct gaa tat gta gtt cca tac atg att cac ctg   3564
Leu Leu Ser Leu Leu Pro Glu Tyr Val Val Pro Tyr Met Ile His Leu
        995                 1000                1005 cta gcc cat gat cca gat ttt aca aga tca caa gat gtt gat cag      3609
Leu Ala His Asp Pro Asp Phe Thr Arg Ser Gln Asp Val Asp Gln
        1010                1015                1020 ctt cgt gat atc aaa gag tgc cta tgg ttc atg ctt gaa gtt tta      3654
Leu Arg Asp Ile Lys Glu Cys Leu Trp Phe Met Leu Glu Val Leu
        1025                1030                1035 atg aca aag aat gaa aac aat agc cat gcc ttt atg aag aag atg      3699
Met Thr Lys Asn Glu Asn Asn Ser His Ala Phe Met Lys Lys Met
        1040                1045                1050 gca gag aac atc aag tta acc aga gat gcc cag tct cca gat gaa      3744
Ala Glu Asn Ile Lys Leu Thr Arg Asp Ala Gln Ser Pro Asp Glu
        1055                1060                1065 tcc aag aca aat gaa aaa ctg tat aca gta tgt gat gtg gct ctc      3789
Ser Lys Thr Asn Glu Lys Leu Tyr Thr Val Cys Asp Val Ala Leu
        1070                1075                1080 tgt gtt ata aat agt aaa agt gct ttg tgc aat gca gat tca cca      3834
Cys Val Ile Asn Ser Lys Ser Ala Leu Cys Asn Ala Asp Ser Pro
        1085                1090                1095 aag gac cca gtc ctc cca atg aaa ttt ttt aca caa cct gaa aag      3879
Lys Asp Pro Val Leu Pro Met Lys Phe Phe Thr Gln Pro Glu Lys
        1100                1105                1110 gac ttc tgt aac gat aag agt tat att tca gaa gag aca aga gta      3924
Asp Phe Cys Asn Asp Lys Ser Tyr Ile Ser Glu Glu Thr Arg Val
        1115                1120                1125 ctt ctg tta aca gga aag cca aag cct gct gga gta cta ggt gca      3969
```

```
                    Leu Leu Leu Thr Gly Lys Pro Lys Pro Ala Gly Val Leu Gly Ala
                    1130                1135                1140 gta aat aag cct tta tca gca acg gga agg aaa ccc tat gtt aga          4014
Val Asn Lys Pro Leu Ser Ala Thr Gly Arg Lys Pro Tyr Val Arg
1145                1150                1155 agc act ggc act gag act gga agc aat att aat gta aat tca gag          4059
Ser Thr Gly Thr Glu Thr Gly Ser Asn Ile Asn Val Asn Ser Glu
    1160                1165                1170 ctg aac cct tca acc gga aat cga tca agg gaa cag agt tca gag          4104
Leu Asn Pro Ser Thr Gly Asn Arg Ser Arg Glu Gln Ser Ser Glu
    1175                1180                1185 gca gca gaa act gga gtt agt gaa aat gaa gag aac cct gtg agg          4149
Ala Ala Glu Thr Gly Val Ser Glu Asn Glu Glu Asn Pro Val Arg
    1190                1195                1200 att att tca gtc aca cct gta aag aat att gac cca gta aag aat          4194
Ile Ile Ser Val Thr Pro Val Lys Asn Ile Asp Pro Val Lys Asn
    1205                1210                1215 aag gaa att aat tct gat cag gct acc cag ggc aac atc agc agt          4239
Lys Glu Ile Asn Ser Asp Gln Ala Thr Gln Gly Asn Ile Ser Ser
    1220                1225                1230 gac cga gga aag aaa aga aca gta aca gca gct ggt gca gag aat          4284
Asp Arg Gly Lys Lys Arg Thr Val Thr Ala Ala Gly Ala Glu Asn
    1235                1240                1245 atc caa caa aaa aca gat gag aaa gta gat gaa tcg gga cct ccc          4329
Ile Gln Gln Lys Thr Asp Glu Lys Val Asp Glu Ser Gly Pro Pro
    1250                1255                1260 gcc cct tcc aaa ccc agg aga gga cgt cga ccc aag tct gaa tct          4374
Ala Pro Ser Lys Pro Arg Arg Gly Arg Arg Pro Lys Ser Glu Ser
    1265                1270                1275 cag ggc aat gct acc aaa aat gat gat cta aat aaa cct att aac          4419
Gln Gly Asn Ala Thr Lys Asn Asp Asp Leu Asn Lys Pro Ile Asn
    1280                1285                1290 aag gga agg aag aga gct gca gtg ggt cag gag agc cct ggg ggt          4464
Lys Gly Arg Lys Arg Ala Ala Val Gly Gln Glu Ser Pro Gly Gly
    1295                1300                1305 ttg gaa gca ggt aat gcc aaa gca ccc aaa ctg caa gat tta gcc          4509
Leu Glu Ala Gly Asn Ala Lys Ala Pro Lys Leu Gln Asp Leu Ala
    1310                1315                1320 aaa aag gca gca cca gca gaa aga caa att gac tta caa agg taa          4554
Lys Lys Ala Ala Pro Ala Glu Arg Gln Ile Asp Leu Gln Arg
    1325                1330                1335 aaatgcattt gcaagggag aaaatgaagg ccaaacagaa gcaggctcca gcttctgcaa      4614
aaacttggat tcacaaatgt ccctgaacag aaaatgaagc tcacttcaga acacacactc      4674
tctgccttga aaactaaaga gactattact tccttttcac atgaccacaa gtcctctgat      4734
ggaaatgtac agcagaaact cttgagagag aggctaaaag caactctgtt ctcccccttc      4794
ccctagactt ttcttacgaa aagtcaataa ttaagcaaat tgcttaacac ttggttccag      4854
ttcctgccta tctggagttt aaatgcgtaa tacaccatta atttccacgc tgcagttttt      4914
attttaaaga aagtaacaag atgtctttac actgacactg aaaattcatc cattttagag      4974
ccaggaattc ccatgttaca caggaaaaaa tagaagtcta ctgaattaat tttttaaaag      5034
aaaagagatc agattaaata tttctttgtt tttccttttg gaaactttta tgtataattc      5094
tttctgcctg cctactttc tgcaaaaatg agatgtacag atttcggttc cctgctatga      5154
aaagtgatgt ggtagcaatt ttataaatgt gctttctga ttttatcag agtgagaaaa      5214 ttaaaattat tgatttgcaa gtagtaaaca gttcatattt tgatttcccc tcatttagt      5274
```

-continued

```
ttaatataat ttgcaataaa tgtacatatt gttgtttgtt tcataaagca tatcacttta    5334
aaatggtttt tactcctgtg attatgttgg aatatttgga attttaaagg agtaaagact    5394
gtccagcatt tggttttata atgtttgtca ccagatttt  attaatgtaa aaaaaatcaa    5454
tttttaaaaa atagttggac tttggcagct tttaaggaaa gttggaggtg ttttaggatt    5514
gctatcaatt ttcagcattg tgctatttgg aaataagtgt tttgcttttg tctgatggtc    5574
tgggctcatt tttatgttta ttttagaaaa ctgttgcatc aatatattat gtttcttggc    5634
attgttcagc ataggtaatg tgtgcacttt atgtgtacac ataatcatat ttaagttttt    5694
tgcataaaat aaatgcttct agatgtcatg gcagtctttt taatcttttt atcatatgct    5754
ttcttgtgaa tttttcatg  ttaaagagct aaagtcataa catgattaca gtcaactctc    5814
cattatctat ataaaatagt gactaagcct caggttttta attttgtgat aacaaaataa    5874
cgaaggcatg taagacctga ttctggagga acatgaaatt tgtctttct  catgtccaga    5934
gttctatcct gcccccactg tccactgtag ggtcatccgc aaagccctag cagaatgtgc    5994
tcactccatt tccttacacg tttctagcat gggtcagagg aaacaacatt tgtgttataa    6054
cttcgtcttg ataggctgta gtgtacatgg gatgtaaaac aaacaagtgt atcaaaggtg    6114
gatgattctg ttagagtgaa gtttgagagt aaatgtcact tacgtttctc atagataatc    6174
aagagttggc tgtgtattga ctgaaagatg ggtaattatt ttaaatatgc atttacacac    6234
atttaggtat cagaagatgc ttagggaaca atggatacca atgatagaaa atgataccttt   6294
tacaggggca gaaaaatccc cactcttcct tattgcctct tcagaaccct ttagaaagta    6354
taaaatattg cctccaacat gctgaaaaag agtatctatg cataagtatc agagaagtcc    6414
ctcaagcaat cagtaggtgt gttctattta gagagagttt aaagttctct tagcatcaga    6474
caacttgatt cctaaggttt ccagtgtgtc accaacaaaa agtgcattga tagggaccttt   6534
tgtctcttcc tcccttgat  taattgcccg gcatcacagt ttactagatt accaagtgtt    6594
acatcatatt aaataaaatg tagcagaacc atctgcatca atatattcct gtttagattt    6654
ttgcaggaga gaagttaaaa ggatttgctc cttgtatgat gtaagtggcc cacccccaatt   6714
ttgtaacatg atgcaagtgt ctggcactaa gggaagcaag agtagggttg tggaaagacc    6774
aagctgatgg ggagggactt gtttacggga atttttttag ttttcctttt caaaggaaaa    6834
cattaaaatc ccttaggaat ttggtattca catctcagag aactacaaca caaaagtgca    6894
gacttatatt tgagaattaa tgttaacccct ttgtgtctag tttgaagctt cttgtatttg    6954
tctaaaacaa caagccagaa ttttgtatct cctttgataa aaagtgtgta taatgtaaag    7014
tagttttgca tattcttgtg ctgcacatgg gctgaatttt taatttttt  ttaaaaactt    7074
gaagcagaac cttgtaattt gtgtaaatga caagtgtaaa atcctaccat aaaatgctaa    7134
aaatatgcac tgtttcaaat aaaaccaaga aatgcagcat taaaaaaaaa aaaaa         7190
```

<210> SEQ ID NO 2
<211> LENGTH: 1337
<212> TYPE: PRT
<213> ORGANISM: Homo sapiens

<400> SEQUENCE: 2

```
Met Asp Phe Thr Ala Gln Pro Lys Pro Ala Thr Ala Leu Cys Gly Val
1               5                   10                  15

Val Ser Ala Asp Gly Lys Ile Ala Tyr Pro Pro Gly Val Lys Glu Ile
            20                  25                  30

Thr Asp Lys Ile Thr Thr Asp Glu Met Ile Lys Arg Leu Lys Met Val
```

```
            35                  40                  45
Val Lys Thr Phe Met Asp Met Asp Gln Asp Ser Glu Asp Glu Lys Gln
 50                  55                  60

Gln Tyr Leu Pro Leu Ala Leu His Leu Ala Ser Glu Phe Phe Leu Arg
 65                  70                  75                  80

Asn Pro Asn Lys Asp Val Arg Leu Leu Val Ala Cys Cys Leu Ala Asp
                 85                  90                  95

Ile Phe Arg Ile Tyr Ala Pro Glu Ala Pro Tyr Thr Ser His Asp Lys
            100                 105                 110

Leu Lys Asp Ile Phe Leu Phe Ile Thr Arg Gln Leu Lys Gly Leu Glu
            115                 120                 125

Asp Thr Lys Ser Pro Gln Phe Asn Arg Tyr Phe Tyr Leu Leu Glu Asn
            130                 135                 140

Leu Ala Trp Val Lys Ser Tyr Asn Ile Cys Phe Glu Leu Glu Asp Cys
145                 150                 155                 160

Asn Glu Ile Phe Ile Gln Leu Phe Arg Thr Leu Phe Ser Val Ile Asn
                165                 170                 175

Asn Ser His Asn Lys Lys Val Gln Met His Met Leu Asp Leu Met Ser
            180                 185                 190

Ser Ile Ile Met Glu Gly Asp Gly Val Thr Gln Glu Leu Leu Asp Ser
            195                 200                 205

Ile Leu Ile Asn Leu Ile Pro Ala His Lys Asn Leu Asn Lys Gln Ser
210                 215                 220

Phe Asp Leu Ala Lys Val Leu Leu Lys Arg Thr Val Gln Thr Ile Glu
225                 230                 235                 240

Ala Cys Ile Ala Asn Phe Phe Asn Gln Val Leu Val Leu Gly Arg Ser
                245                 250                 255

Ser Val Ser Asp Leu Ser Glu His Val Phe Asp Leu Ile Gln Glu Leu
            260                 265                 270

Phe Ala Ile Asp Pro His Leu Leu Leu Ser Val Met Pro Gln Leu Glu
            275                 280                 285

Phe Lys Leu Lys Ser Asn Asp Gly Glu Glu Arg Leu Ala Val Val Arg
            290                 295                 300

Leu Leu Ala Lys Leu Phe Gly Ser Lys Asp Ser Asp Leu Ala Thr Gln
305                 310                 315                 320

Asn Arg Pro Leu Trp Gln Cys Phe Leu Gly Arg Phe Asn Asp Ile His
                325                 330                 335

Val Pro Val Arg Leu Glu Ser Val Lys Phe Ala Ser His Cys Leu Met
            340                 345                 350

Asn His Pro Asp Leu Ala Lys Asp Leu Thr Glu Tyr Leu Lys Val Arg
            355                 360                 365

Ser His Asp Pro Glu Glu Ala Ile Arg His Asp Val Ile Val Thr Ile
            370                 375                 380

Ile Thr Ala Ala Lys Arg Asp Leu Ala Leu Val Asn Asp Gln Leu Leu
385                 390                 395                 400

Gly Phe Val Arg Glu Arg Thr Leu Asp Lys Arg Trp Arg Val Arg Lys
                405                 410                 415

Glu Ala Met Met Gly Leu Ala Gln Leu Tyr Lys Lys Tyr Cys Leu His
            420                 425                 430

Gly Glu Ala Gly Lys Glu Ala Ala Glu Lys Val Ser Trp Ile Lys Asp
            435                 440                 445

Lys Leu Leu His Ile Tyr Tyr Gln Asn Ser Ile Asp Asp Lys Leu Leu
450                 455                 460
```

```
Val Glu Lys Ile Phe Ala Gln Tyr Leu Val Pro His Asn Leu Glu Thr
465                 470                 475                 480

Glu Glu Arg Met Lys Cys Leu Tyr Tyr Leu Tyr Ala Ser Leu Asp Pro
                485                 490                 495

Asn Ala Val Lys Ala Leu Asn Glu Met Trp Lys Cys Gln Asn Met Leu
            500                 505                 510

Arg Ser His Val Arg Glu Leu Leu Asp Leu His Lys Gln Pro Thr Ser
        515                 520                 525

Glu Ala Asn Cys Ser Ala Met Phe Gly Lys Leu Met Thr Ile Ala Lys
    530                 535                 540

Asn Leu Pro Asp Pro Gly Lys Ala Gln Asp Phe Val Lys Lys Phe Asn
545                 550                 555                 560

Gln Val Leu Gly Asp Asp Glu Lys Leu Arg Ser Gln Leu Glu Leu Leu
                565                 570                 575

Ile Ser Pro Thr Cys Ser Cys Lys Gln Ala Asp Ile Cys Val Arg Glu
            580                 585                 590

Ile Ala Arg Lys Leu Ala Asn Pro Lys Gln Pro Thr Asn Pro Phe Leu
        595                 600                 605

Glu Met Val Lys Phe Leu Leu Glu Arg Ile Ala Pro Val His Ile Asp
    610                 615                 620

Ser Glu Ala Ile Ser Ala Leu Val Lys Leu Met Asn Lys Ser Ile Glu
625                 630                 635                 640

Gly Thr Ala Asp Asp Glu Glu Glu Gly Val Ser Pro Asp Thr Ala Ile
                645                 650                 655

Arg Ser Gly Leu Glu Leu Leu Lys Val Leu Ser Phe Thr His Pro Thr
            660                 665                 670

Ser Phe His Ser Ala Glu Thr Tyr Glu Ser Leu Leu Gln Cys Leu Arg
        675                 680                 685

Met Glu Asp Asp Lys Val Ala Glu Ala Ala Ile Gln Ile Phe Arg Asn
    690                 695                 700

Thr Gly His Lys Ile Glu Thr Asp Leu Pro Gln Ile Arg Ser Thr Leu
705                 710                 715                 720

Ile Pro Ile Leu His Gln Lys Ala Lys Arg Gly Thr Pro His Gln Ala
                725                 730                 735

Lys Gln Ala Val His Cys Ile His Ala Ile Phe Thr Asn Lys Glu Val
            740                 745                 750

Gln Leu Ala Gln Ile Phe Glu Pro Leu Ser Arg Ser Leu Asn Ala Asp
        755                 760                 765

Val Pro Glu Gln Leu Ile Thr Pro Leu Val Ser Leu Gly His Ile Ser
    770                 775                 780

Met Leu Ala Pro Asp Gln Phe Ala Ser Pro Met Lys Ser Val Val Ala
785                 790                 795                 800

Asn Phe Ile Val Lys Asp Leu Leu Met Asn Asp Arg Ser Thr Gly Glu
                805                 810                 815

Lys Asn Gly Lys Leu Trp Ser Pro Asp Glu Val Ser Pro Glu Val
            820                 825                 830

Leu Ala Lys Val Gln Ala Ile Lys Leu Leu Val Arg Trp Leu Leu Gly
        835                 840                 845

Met Lys Asn Asn Gln Ser Lys Ser Ala Asn Ser Thr Leu Arg Leu Leu
    850                 855                 860

Ser Ala Met Leu Val Ser Glu Gly Asp Leu Thr Glu Gln Lys Arg Ile
865                 870                 875                 880
```

```
Ser Lys Ser Asp Met Ser Arg Leu Arg Leu Ala Ala Gly Ser Ala Ile
                885                 890                 895
Met Lys Leu Ala Gln Glu Pro Cys Tyr His Glu Ile Ile Thr Pro Glu
            900                 905                 910
Gln Phe Gln Leu Cys Ala Leu Val Ile Asn Asp Glu Cys Tyr Gln Val
            915                 920                 925
Arg Gln Ile Phe Ala Gln Lys Leu His Lys Ala Leu Val Lys Leu Leu
            930                 935                 940
Leu Pro Leu Glu Tyr Met Ala Ile Phe Ala Leu Cys Ala Lys Asp Pro
945                 950                 955                 960
Val Lys Glu Arg Arg Ala His Ala Arg Gln Cys Leu Leu Lys Asn Ile
            965                 970                 975
Ser Ile Arg Arg Glu Tyr Ile Lys Gln Asn Pro Met Ala Thr Glu Lys
            980                 985                 990
Leu Leu Ser Leu Leu Pro Glu Tyr Val Val Pro Tyr Met Ile His Leu
            995                 1000                1005
Leu Ala His Asp Pro Asp Phe Thr Arg Ser Gln Asp Val Asp Gln
            1010                1015                1020
Leu Arg Asp Ile Lys Glu Cys Leu Trp Phe Met Leu Glu Val Leu
            1025                1030                1035
Met Thr Lys Asn Glu Asn Asn Ser His Ala Phe Met Lys Lys Met
            1040                1045                1050
Ala Glu Asn Ile Lys Leu Thr Arg Asp Ala Gln Ser Pro Asp Glu
            1055                1060                1065
Ser Lys Thr Asn Glu Lys Leu Tyr Thr Val Cys Asp Val Ala Leu
            1070                1075                1080
Cys Val Ile Asn Ser Lys Ser Ala Leu Cys Asn Ala Asp Ser Pro
            1085                1090                1095
Lys Asp Pro Val Leu Pro Met Lys Phe Phe Thr Gln Pro Glu Lys
            1100                1105                1110
Asp Phe Cys Asn Asp Lys Ser Tyr Ile Ser Glu Glu Thr Arg Val
            1115                1120                1125
Leu Leu Leu Thr Gly Lys Pro Lys Pro Ala Gly Val Leu Gly Ala
            1130                1135                1140
Val Asn Lys Pro Leu Ser Ala Thr Gly Arg Lys Pro Tyr Val Arg
            1145                1150                1155
Ser Thr Gly Thr Glu Thr Gly Ser Asn Ile Asn Val Asn Ser Glu
            1160                1165                1170
Leu Asn Pro Ser Thr Gly Asn Arg Ser Arg Glu Gln Ser Ser Glu
            1175                1180                1185
Ala Ala Glu Thr Gly Val Ser Glu Asn Glu Glu Asn Pro Val Arg
            1190                1195                1200
Ile Ile Ser Val Thr Pro Val Lys Asn Ile Asp Pro Val Lys Asn
            1205                1210                1215
Lys Glu Ile Asn Ser Asp Gln Ala Thr Gln Gly Asn Ile Ser Ser
            1220                1225                1230
Asp Arg Gly Lys Lys Arg Thr Val Thr Ala Ala Gly Ala Glu Asn
            1235                1240                1245
Ile Gln Gln Lys Thr Asp Glu Lys Val Asp Glu Ser Gly Pro Pro
            1250                1255                1260
Ala Pro Ser Lys Pro Arg Arg Gly Arg Arg Pro Lys Ser Glu Ser
            1265                1270                1275
Gln Gly Asn Ala Thr Lys Asn Asp Asp Leu Asn Lys Pro Ile Asn
```

```
                     1280                1285                1290
Lys Gly  Arg Lys Arg Ala  Ala  Val Gly Gln Glu  Ser Pro Gly Gly
         1295                1300                1305

Leu Glu  Ala Gly Asn Ala  Lys  Ala Pro Lys Leu  Gln Asp Leu Ala
         1310                1315                1320

Lys Lys  Ala Ala Pro Ala  Glu  Arg Gln Ile Asp  Leu Gln Arg
         1325                1330                1335
```

<210> SEQ ID NO 3
<211> LENGTH: 9
<212> TYPE: PRT
<213> ORGANISM: Homo sapiens

<400> SEQUENCE: 3

```
Tyr Leu Pro Leu Ala Leu His Leu Ala
1               5
```

<210> SEQ ID NO 4
<211> LENGTH: 10
<212> TYPE: PRT
<213> ORGANISM: Homo sapiens

<400> SEQUENCE: 4

```
Leu Leu Val Ala Cys Cys Leu Ala Asp Ile
1               5                   10
```

<210> SEQ ID NO 5
<211> LENGTH: 9
<212> TYPE: PRT
<213> ORGANISM: Homo sapiens

<400> SEQUENCE: 5

```
Tyr Leu Leu Glu Asn Leu Ala Trp Val
1               5
```

<210> SEQ ID NO 6
<211> LENGTH: 9
<212> TYPE: PRT
<213> ORGANISM: Homo sapiens

<400> SEQUENCE: 6

```
Gln Leu Phe Arg Thr Leu Phe Ser Val
1               5
```

<210> SEQ ID NO 7
<211> LENGTH: 9
<212> TYPE: PRT
<213> ORGANISM: Homo sapiens

<400> SEQUENCE: 7

```
Leu Leu Asp Ser Ile Leu Ile Asn Leu
1               5
```

<210> SEQ ID NO 8
<211> LENGTH: 10
<212> TYPE: PRT
<213> ORGANISM: Homo sapiens

<400> SEQUENCE: 8

```
Ala Ile Asp Pro His Leu Leu Leu Ser Val
1               5                   10
```

<210> SEQ ID NO 9

```
<211> LENGTH: 9
<212> TYPE: PRT
<213> ORGANISM: Homo sapiens

<400> SEQUENCE: 9

Tyr Leu Val Pro His Asn Leu Glu Thr
1               5

<210> SEQ ID NO 10
<211> LENGTH: 10
<212> TYPE: PRT
<213> ORGANISM: Homo sapiens

<400> SEQUENCE: 10

Tyr Leu Tyr Ala Ser Leu Asp Pro Asn Ala
1               5                   10

<210> SEQ ID NO 11
<211> LENGTH: 9
<212> TYPE: PRT
<213> ORGANISM: Homo sapiens

<400> SEQUENCE: 11

Ala Met Phe Gly Lys Leu Met Thr Ile
1               5

<210> SEQ ID NO 12
<211> LENGTH: 9
<212> TYPE: PRT
<213> ORGANISM: Homo sapiens

<400> SEQUENCE: 12

Phe Leu Leu Glu Arg Ile Ala Pro Val
1               5

<210> SEQ ID NO 13
<211> LENGTH: 9
<212> TYPE: PRT
<213> ORGANISM: Homo sapiens

<400> SEQUENCE: 13

Leu Asn Ala Asp Val Pro Glu Gln Leu
1               5

<210> SEQ ID NO 14
<211> LENGTH: 8
<212> TYPE: PRT
<213> ORGANISM: Homo sapiens

<400> SEQUENCE: 14

Gln Leu Ile Thr Pro Leu Val Ser
1               5

<210> SEQ ID NO 15
<211> LENGTH: 10
<212> TYPE: PRT
<213> ORGANISM: Homo sapiens

<400> SEQUENCE: 15

Lys Leu Trp Ser Pro Asp Glu Glu Val Ser
1               5                   10

<210> SEQ ID NO 16
<211> LENGTH: 9
<212> TYPE: PRT
```

<213> ORGANISM: Homo sapiens

<400> SEQUENCE: 16

Val Ile Asn Asp Glu Cys Tyr Gln Val
1               5

<210> SEQ ID NO 17
<211> LENGTH: 9
<212> TYPE: PRT
<213> ORGANISM: Homo sapiens

<400> SEQUENCE: 17

Tyr Met Ala Ile Phe Ala Leu Cys Ala
1               5

<210> SEQ ID NO 18
<211> LENGTH: 10
<212> TYPE: PRT
<213> ORGANISM: Homo sapiens

<400> SEQUENCE: 18

Lys Leu Tyr Thr Val Cys Asp Val Ala Leu
1               5                   10

<210> SEQ ID NO 19
<211> LENGTH: 10
<212> TYPE: PRT
<213> ORGANISM: Homo sapiens

<400> SEQUENCE: 19

Tyr Thr Val Cys Asp Val Ala Leu Cys Val
1               5                   10

<210> SEQ ID NO 20
<211> LENGTH: 9
<212> TYPE: PRT
<213> ORGANISM: Homo sapiens

<400> SEQUENCE: 20

Ala Tyr Pro Pro Gly Val Lys Glu Ile
1               5

<210> SEQ ID NO 21
<211> LENGTH: 9
<212> TYPE: PRT
<213> ORGANISM: Homo sapiens

<400> SEQUENCE: 21

Gln Tyr Leu Pro Leu Ala Leu His Leu
1               5

<210> SEQ ID NO 22
<211> LENGTH: 9
<212> TYPE: PRT
<213> ORGANISM: Homo sapiens

<400> SEQUENCE: 22

Ile Phe Leu Phe Ile Thr Arg Gln Leu
1               5

<210> SEQ ID NO 23
<211> LENGTH: 9
<212> TYPE: PRT
<213> ORGANISM: Homo sapiens

```
<400> SEQUENCE: 23

Gln Phe Asn Arg Tyr Phe Tyr Leu Leu
1               5

<210> SEQ ID NO 24
<211> LENGTH: 9
<212> TYPE: PRT
<213> ORGANISM: Homo sapiens

<400> SEQUENCE: 24

Arg Tyr Phe Tyr Leu Leu Glu Asn Leu
1               5

<210> SEQ ID NO 25
<211> LENGTH: 9
<212> TYPE: PRT
<213> ORGANISM: Homo sapiens

<400> SEQUENCE: 25

Phe Tyr Leu Leu Glu Asn Leu Ala Trp
1               5

<210> SEQ ID NO 26
<211> LENGTH: 10
<212> TYPE: PRT
<213> ORGANISM: Homo sapiens

<400> SEQUENCE: 26

Ala Trp Val Lys Ser Tyr Asn Ile Cys Phe
1               5                   10

<210> SEQ ID NO 27
<211> LENGTH: 9
<212> TYPE: PRT
<213> ORGANISM: Homo sapiens

<400> SEQUENCE: 27

Ile Phe Ile Gln Leu Phe Arg Thr Leu
1               5

<210> SEQ ID NO 28
<211> LENGTH: 9
<212> TYPE: PRT
<213> ORGANISM: Homo sapiens

<400> SEQUENCE: 28

Val Phe Asp Leu Ile Gln Glu Leu Phe
1               5

<210> SEQ ID NO 29
<211> LENGTH: 9
<212> TYPE: PRT
<213> ORGANISM: Homo sapiens

<400> SEQUENCE: 29

Leu Phe Ala Ile Asp Pro His Leu Leu
1               5

<210> SEQ ID NO 30
<211> LENGTH: 9
<212> TYPE: PRT
<213> ORGANISM: Homo sapiens

<400> SEQUENCE: 30
```

```
Leu Trp Gln Cys Phe Leu Gly Arg Phe
1               5
```

```
<210> SEQ ID NO 31
<211> LENGTH: 10
<212> TYPE: PRT
<213> ORGANISM: Homo sapiens

<400> SEQUENCE: 31

Tyr Tyr Gln Asn Ser Ile Asp Asp Lys Leu
1               5                   10
```

```
<210> SEQ ID NO 32
<211> LENGTH: 9
<212> TYPE: PRT
<213> ORGANISM: Homo sapiens

<400> SEQUENCE: 32

Thr Tyr Glu Ser Leu Leu Gln Cys Leu
1               5
```

```
<210> SEQ ID NO 33
<211> LENGTH: 9
<212> TYPE: PRT
<213> ORGANISM: Homo sapiens

<400> SEQUENCE: 33

Ile Phe Arg Asn Thr Gly His Lys Ile
1               5
```

```
<210> SEQ ID NO 34
<211> LENGTH: 9
<212> TYPE: PRT
<213> ORGANISM: Homo sapiens

<400> SEQUENCE: 34

Ile Phe Glu Pro Leu Ser Arg Ser Leu
1               5
```

```
<210> SEQ ID NO 35
<211> LENGTH: 16
<212> TYPE: PRT
<213> ORGANISM: Homo sapiens

<400> SEQUENCE: 35

Ala Ser Glu Phe Phe Leu Arg Asn Pro Asn Lys Asp Val Arg Leu Leu
1               5                   10                  15
```

```
<210> SEQ ID NO 36
<211> LENGTH: 19
<212> TYPE: PRT
<213> ORGANISM: Homo sapiens

<400> SEQUENCE: 36

Leu Lys Asp Ile Phe Leu Phe Ile Thr Arg Gln Leu Lys Gly Leu Glu
1               5                   10                  15

Asp Thr Lys
```

```
<210> SEQ ID NO 37
<211> LENGTH: 17
<212> TYPE: PRT
<213> ORGANISM: Homo sapiens

<400> SEQUENCE: 37
```

```
Phe Asn Arg Tyr Phe Tyr Leu Leu Glu Asn Leu Ala Trp Val Lys Ser
1               5                   10                  15

Tyr

<210> SEQ ID NO 38
<211> LENGTH: 15
<212> TYPE: PRT
<213> ORGANISM: Homo sapiens

<400> SEQUENCE: 38

Asn Leu Ala Trp Val Lys Ser Tyr Asn Ile Cys Phe Glu Leu Glu
1               5                   10                  15

<210> SEQ ID NO 39
<211> LENGTH: 18
<212> TYPE: PRT
<213> ORGANISM: Homo sapiens

<400> SEQUENCE: 39

Asn Glu Ile Phe Ile Gln Leu Phe Arg Thr Leu Phe Ser Val Ile Asn
1               5                   10                  15

Asn Ser

<210> SEQ ID NO 40
<211> LENGTH: 17
<212> TYPE: PRT
<213> ORGANISM: Homo sapiens

<400> SEQUENCE: 40

Thr Leu Phe Ser Val Ile Asn Asn Ser His Asn Lys Lys Val Gln Met
1               5                   10                  15

His

<210> SEQ ID NO 41
<211> LENGTH: 18
<212> TYPE: PRT
<213> ORGANISM: Homo sapiens

<400> SEQUENCE: 41

Asn Lys Lys Val Gln Met His Met Leu Asp Leu Met Ser Ser Ile Ile
1               5                   10                  15

Met Glu

<210> SEQ ID NO 42
<211> LENGTH: 19
<212> TYPE: PRT
<213> ORGANISM: Homo sapiens

<400> SEQUENCE: 42

Leu Asp Ser Ile Leu Ile Asn Leu Ile Pro Ala His Lys Asn Leu Asn
1               5                   10                  15

Lys Gln Ser

<210> SEQ ID NO 43
<211> LENGTH: 23
<212> TYPE: PRT
<213> ORGANISM: Homo sapiens

<400> SEQUENCE: 43

Ile Gln Glu Leu Phe Ala Ile Asp Pro His Leu Leu Leu Ser Val Met
1               5                   10                  15
```

Pro Gln Leu Glu Phe Lys Leu
            20

<210> SEQ ID NO 44
<211> LENGTH: 18
<212> TYPE: PRT
<213> ORGANISM: Homo sapiens

<400> SEQUENCE: 44

Gly Glu Glu Arg Leu Ala Val Val Arg Leu Leu Ala Lys Leu Phe Gly
1               5                   10                  15

Ser Lys

<210> SEQ ID NO 45
<211> LENGTH: 19
<212> TYPE: PRT
<213> ORGANISM: Homo sapiens

<400> SEQUENCE: 45

His Asp Val Ile Val Thr Ile Ile Thr Ala Ala Lys Arg Asp Leu Ala
1               5                   10                  15

Leu Val Asn

<210> SEQ ID NO 46
<211> LENGTH: 19
<212> TYPE: PRT
<213> ORGANISM: Homo sapiens

<400> SEQUENCE: 46

Ser Ala Met Phe Gly Lys Leu Met Thr Ile Ala Lys Asn Leu Pro Asp
1               5                   10                  15

Pro Gly Lys

<210> SEQ ID NO 47
<211> LENGTH: 16
<212> TYPE: PRT
<213> ORGANISM: Homo sapiens

<400> SEQUENCE: 47

Ala Gln Asp Phe Val Lys Lys Phe Asn Gln Val Leu Gly Asp Asp Glu
1               5                   10                  15

<210> SEQ ID NO 48
<211> LENGTH: 21
<212> TYPE: PRT
<213> ORGANISM: Homo sapiens

<400> SEQUENCE: 48

Glu Cys Leu Glu Ala Ile Ser Ala Leu Val Lys Leu Met Asn Lys Ser
1               5                   10                  15

Ile Glu Gly Thr Ala
            20

<210> SEQ ID NO 49
<211> LENGTH: 15
<212> TYPE: PRT
<213> ORGANISM: Homo sapiens

<400> SEQUENCE: 49

Pro Thr Ser Phe His Ser Ala Glu Thr Tyr Glu Ser Leu Leu Gln
1               5                   10                  15

```
<210> SEQ ID NO 50
<211> LENGTH: 18
<212> TYPE: PRT
<213> ORGANISM: Homo sapiens

<400> SEQUENCE: 50

Glu Ala Ala Ile Gln Ile Phe Arg Asn Thr Gly His Lys Ile Glu Thr
1               5                   10                  15

Asp Leu

<210> SEQ ID NO 51
<211> LENGTH: 18
<212> TYPE: PRT
<213> ORGANISM: Homo sapiens

<400> SEQUENCE: 51

Leu Pro Gln Ile Arg Ser Thr Leu Ile Pro Ile Leu His Gln Lys Ala
1               5                   10                  15

Lys Arg

<210> SEQ ID NO 52
<211> LENGTH: 16
<212> TYPE: PRT
<213> ORGANISM: Homo sapiens

<400> SEQUENCE: 52

Leu Ile Pro Ile Leu His Gln Lys Ala Lys Arg Gly Thr Pro His Gln
1               5                   10                  15

<210> SEQ ID NO 53
<211> LENGTH: 20
<212> TYPE: PRT
<213> ORGANISM: Homo sapiens

<400> SEQUENCE: 53

Lys Gln Ala Val His Cys Ile His Ala Ile Phe Thr Asn Lys Glu Val
1               5                   10                  15

Gln Leu Ala Gln
            20

<210> SEQ ID NO 54
<211> LENGTH: 15
<212> TYPE: PRT
<213> ORGANISM: Homo sapiens

<400> SEQUENCE: 54

Ala Ser Pro Met Lys Ser Val Val Ala Asn Phe Ile Val Lys Asp
1               5                   10                  15

<210> SEQ ID NO 55
<211> LENGTH: 19
<212> TYPE: PRT
<213> ORGANISM: Homo sapiens

<400> SEQUENCE: 55

Val Leu Ala Lys Val Gln Ala Ile Lys Leu Leu Val Arg Trp Leu Leu
1               5                   10                  15

Gly Met Lys

<210> SEQ ID NO 56
<211> LENGTH: 18
<212> TYPE: PRT
<213> ORGANISM: Homo sapiens
```

<400> SEQUENCE: 56

Lys Leu Leu Val Arg Trp Leu Leu Gly Met Lys Asn Asn Gln Ser Lys
1               5                   10                  15

Ser Ala

<210> SEQ ID NO 57
<211> LENGTH: 20
<212> TYPE: PRT
<213> ORGANISM: Homo sapiens

<400> SEQUENCE: 57

Ser Ala Asn Ser Thr Leu Arg Leu Leu Ser Ala Met Leu Val Ser Glu
1               5                   10                  15

Gly Asp Leu Thr
            20

<210> SEQ ID NO 58
<211> LENGTH: 18
<212> TYPE: PRT
<213> ORGANISM: Homo sapiens

<400> SEQUENCE: 58

Lys Ser Asp Met Ser Arg Leu Arg Leu Ala Ala Gly Ser Ala Ile Met
1               5                   10                  15

Lys Leu

<210> SEQ ID NO 59
<211> LENGTH: 19
<212> TYPE: PRT
<213> ORGANISM: Homo sapiens

<400> SEQUENCE: 59

Cys Tyr Gln Val Arg Gln Ile Phe Ala Gln Lys Leu His Lys Ala Leu
1               5                   10                  15

Val Lys Leu

<210> SEQ ID NO 60
<211> LENGTH: 15
<212> TYPE: PRT
<213> ORGANISM: Homo sapiens

<400> SEQUENCE: 60

Pro Leu Glu Tyr Met Ala Ile Phe Ala Leu Cys Ala Lys Asp Pro
1               5                   10                  15

<210> SEQ ID NO 61
<211> LENGTH: 18
<212> TYPE: PRT
<213> ORGANISM: Homo sapiens

<400> SEQUENCE: 61

Ala His Ala Arg Gln Cys Leu Leu Lys Asn Ile Ser Ile Arg Arg Glu
1               5                   10                  15

Tyr Ile

<210> SEQ ID NO 62
<211> LENGTH: 15
<212> TYPE: PRT
<213> ORGANISM: Homo sapiens

<400> SEQUENCE: 62

Arg Arg Glu Tyr Ile Lys Gln Asn Pro Met Ala Thr Glu Lys Leu
1               5                   10                  15

<210> SEQ ID NO 63
<211> LENGTH: 22
<212> TYPE: PRT
<213> ORGANISM: Homo sapiens

<400> SEQUENCE: 63

Glu Cys Leu Trp Phe Met Leu Glu Val Leu Met Thr Lys Asn Glu Asn
1               5                   10                  15

Asn Ser His Ala Phe Met
            20

<210> SEQ ID NO 64
<211> LENGTH: 23
<212> TYPE: PRT
<213> ORGANISM: Homo sapiens

<400> SEQUENCE: 64

Ser His Ala Phe Met Lys Lys Met Ala Glu Asn Ile Lys Leu Thr Arg
1               5                   10                  15

Asp Ala Gln Ser Pro Asp Glu
            20

<210> SEQ ID NO 65
<211> LENGTH: 23
<212> TYPE: PRT
<213> ORGANISM: Homo sapiens

<400> SEQUENCE: 65

Lys Ser Tyr Ile Ser Glu Glu Thr Arg Val Leu Leu Leu Thr Gly Lys
1               5                   10                  15

Pro Lys Pro Ala Gly Val Leu
            20

<210> SEQ ID NO 66
<211> LENGTH: 18
<212> TYPE: PRT
<213> ORGANISM: Homo sapiens

<400> SEQUENCE: 66

Pro Ala Gly Val Leu Gly Ala Val Asn Lys Pro Leu Ser Ala Thr Gly
1               5                   10                  15

Arg Lys

<210> SEQ ID NO 67
<211> LENGTH: 17
<212> TYPE: PRT
<213> ORGANISM: Homo sapiens

<400> SEQUENCE: 67

Glu Asn Pro Val Arg Ile Ile Ser Val Thr Pro Val Lys Asn Ile Asp
1               5                   10                  15

Pro

<210> SEQ ID NO 68
<211> LENGTH: 21
<212> TYPE: DNA
<213> ORGANISM: Artificial
<220> FEATURE:
<223> OTHER INFORMATION: primer sense -continued

```
<400> SEQUENCE: 68
gtaaggtggc tgttgggtat g                                            21

<210> SEQ ID NO 69
<211> LENGTH: 24
<212> TYPE: DNA
<213> ORGANISM: Artificial
<220> FEATURE:
<223> OTHER INFORMATION: primer antisense

<400> SEQUENCE: 69
ggctagcagg tgaatcatgt atgg                                         24

<210> SEQ ID NO 70
<211> LENGTH: 18
<212> TYPE: DNA
<213> ORGANISM: Artificial
<220> FEATURE:
<223> OTHER INFORMATION: GAPDH primer

<400> SEQUENCE: 70
gggctgcttt taactctg                                                18

<210> SEQ ID NO 71
<211> LENGTH: 18
<212> TYPE: DNA
<213> ORGANISM: Artificial
<220> FEATURE:
<223> OTHER INFORMATION: GAPDH primer

<400> SEQUENCE: 71
ccaggaaatg agcttgac                                                18

<210> SEQ ID NO 72
<211> LENGTH: 29
<212> TYPE: DNA
<213> ORGANISM: Artificial
<220> FEATURE:
<223> OTHER INFORMATION: primer sense

<400> SEQUENCE: 72
gcggccgcat ggacttcacc gcgcagccc                                    29

<210> SEQ ID NO 73
<211> LENGTH: 29
<212> TYPE: DNA
<213> ORGANISM: Artificial
<220> FEATURE:
<223> OTHER INFORMATION: primer antisense

<400> SEQUENCE: 73
ctcgagttac ctttgtaagt caatttgtc                                    29

<210> SEQ ID NO 74
<211> LENGTH: 9
<212> TYPE: PRT
<213> ORGANISM: Homo sapiens

<400> SEQUENCE: 74

Ser Leu Tyr Asn Thr Tyr Ala Thr Leu
1               5

<210> SEQ ID NO 75
<211> LENGTH: 9
```

<212> TYPE: PRT
<213> ORGANISM: Homo sapiens

<400> SEQUENCE: 75

Asn Leu Ile Pro Ala His Lys Asn Leu
1               5

<210> SEQ ID NO 76
<211> LENGTH: 10
<212> TYPE: PRT
<213> ORGANISM: Homo sapiens

<400> SEQUENCE: 76

Lys Glu Cys Leu Trp Phe Met Leu Glu Val
1               5                   10

<210> SEQ ID NO 77
<211> LENGTH: 10
<212> TYPE: PRT
<213> ORGANISM: Homo sapiens

<400> SEQUENCE: 77

Phe Leu Gly Arg Phe Asn Asp Ile His Val
1               5                   10

<210> SEQ ID NO 78
<211> LENGTH: 10
<212> TYPE: PRT
<213> ORGANISM: Homo sapiens

<400> SEQUENCE: 78

Leu Leu Leu Pro Leu Glu Tyr Met Ala Ile
1               5                   10

<210> SEQ ID NO 79
<211> LENGTH: 10
<212> TYPE: PRT
<213> ORGANISM: Homo sapiens

<400> SEQUENCE: 79

Ser Leu Asp Pro Asn Ala Val Lys Ala Leu
1               5                   10

<210> SEQ ID NO 80
<211> LENGTH: 9
<212> TYPE: PRT
<213> ORGANISM: Homo sapiens

<400> SEQUENCE: 80

Lys Leu Lys Asp Ile Phe Leu Phe Ile
1               5

<210> SEQ ID NO 81
<211> LENGTH: 10
<212> TYPE: PRT
<213> ORGANISM: Homo sapiens

<400> SEQUENCE: 81

Leu Leu Ser Leu Leu Pro Glu Tyr Val Val
1               5                   10

<210> SEQ ID NO 82
<211> LENGTH: 9
<212> TYPE: PRT
<213> ORGANISM: Homo sapiens

<400> SEQUENCE: 82

Lys Met Ala Glu Asn Ile Lys Leu Thr
1               5

<210> SEQ ID NO 83
<211> LENGTH: 10
<212> TYPE: PRT
<213> ORGANISM: Homo sapiens

<400> SEQUENCE: 83

Gln Val Leu Val Leu Gly Arg Ser Ser Val
1               5                   10

<210> SEQ ID NO 84
<211> LENGTH: 9
<212> TYPE: PRT
<213> ORGANISM: Homo sapiens

<400> SEQUENCE: 84

Arg Tyr Leu Arg Asp Gln Gln Leu Leu
1               5

<210> SEQ ID NO 85
<211> LENGTH: 18
<212> TYPE: PRT
<213> ORGANISM: Homo sapiens

<400> SEQUENCE: 85

Tyr Val Asp Arg Phe Phe Lys Thr Leu Arg Ala Glu Gln Ala Thr Gln
1               5                   10                  15

Asp Val

<210> SEQ ID NO 86
<211> LENGTH: 4
<212> TYPE: PRT
<213> ORGANISM: Homo sapiens

<400> SEQUENCE: 86

Asn Lys Arg Lys
1